(12) United States Patent
Wilke et al.

(10) Patent No.: US 11,000,272 B2
(45) Date of Patent: *May 11, 2021

(54) WOUND CLOSURE SYSTEM

(71) Applicant: WOUND CARE TECHNOLOGIES, INC., Chanhassen, MN (US)

(72) Inventors: Robert C. Wilke, Eden Prairie, MN (US); Paul J. Anderson, Eden Prairie, MN (US); Douglas Duchon, Chanhassen, MN (US)

(73) Assignee: WOUND CARE TECHNOLOGIES, INC., Chanhassen, MN (US)

(*) Notice: Subject to any disclaimer, the term of this patent is extended or adjusted under 35 U.S.C. 154(b) by 216 days.

This patent is subject to a terminal disclaimer.

(21) Appl. No.: 16/236,823

(22) Filed: Dec. 31, 2018

(65) Prior Publication Data
US 2019/0133576 A1    May 9, 2019

Related U.S. Application Data

(63) Continuation of application No. 12/839,156, filed on Jul. 19, 2010, now Pat. No. 10,166,021.

(51) Int. Cl.
*A61B 17/06* (2006.01)
*A61B 17/04* (2006.01)

(52) U.S. Cl.
CPC .. *A61B 17/06123* (2013.01); *A61B 17/06166* (2013.01); *A61B 2017/0496* (2013.01); *A61B 2017/06019* (2013.01); *A61B 2017/06057* (2013.01); *A61B 2017/06176* (2013.01)

(58) Field of Classification Search
CPC . A61B 17/04; A61B 17/0466; A61B 17/0496; A61B 17/08; A61B 2017/0412; A61B 2017/0427; A61B 2017/0472; A61B 2017/081; A61B 2017/086; A61B 2017/1142; A61B 90/02
See application file for complete search history.

(56) References Cited

U.S. PATENT DOCUMENTS

| 10,166,021 B2 * | 1/2019 | Wilke ............. A61B 17/06166 |
| 2001/0018592 A1 | 8/2001 | Schaller et al. |
| 2001/0047181 A1 | 11/2001 | Ho et al. |
| 2003/0092969 A1 | 5/2003 | O'Malley et al. |
| 2003/0149447 A1 | 8/2003 | Morency et al. |

(Continued)

OTHER PUBLICATIONS

Canica® design brochure, "Canica Wound Closure System," © Canica Design, 2004 (5 pages).

(Continued)

*Primary Examiner* — Robert A Lynch
(74) *Attorney, Agent, or Firm* — K&L Gates LLP

(57) ABSTRACT

A wound closure system and a method of reducing the size of an open wound are disclosed. A suture line is sutured through body tissue adjacent an open wound, the suture line sutured so as to pass into the body tissue at an entry point and exit at an exit point, the suture line including a plurality of barbs extending outwardly at an acute angle with respect to a surface of the suture line. A biasing member applies a continuous pulling force on the suture line for stretching the body tissue toward the open wound, wherein the biasing member is configured to take up any slack of the suture line during stretching of the body tissue and keep the suture line taut.

20 Claims, 28 Drawing Sheets

(56) References Cited

U.S. PATENT DOCUMENTS

| | | | |
|---|---|---|---|
| 2003/0163160 A1 | 8/2003 | O'Malley et al. | |
| 2005/0131430 A1 | 6/2005 | Ravikumar | |
| 2005/0192599 A1 | 9/2005 | Demarais | |
| 2006/0095076 A1* | 5/2006 | Elliott | A61B 90/02 606/216 |
| 2007/0208377 A1* | 9/2007 | Kaplan | A61B 17/00234 606/228 |
| 2008/0097483 A1 | 4/2008 | Ortiz et al. | |
| 2009/0018578 A1 | 1/2009 | Wilke et al. | |
| 2010/0185236 A1 | 7/2010 | Elliot et al. | |

OTHER PUBLICATIONS

Topical Hyperbaric Oxygen™ Therapy, "Healing Difficult Wounds," http://www.gwnnedical.com, 3 pages (date printed: Apr. 28, 2004).

Progressive Surgical Products Inc. brochure, "External Tissue Expansion," PROXIDERM™, Copyright 1997 (3 pages).

"History of Wound Care," http://www.proxiderm.com/html/intro2.html, 3 pages (date printed: Jul. 28, 2004).

"Proxiderm Procedure," http://www.proxiderm.com/html/intro3.html, 2 pages (date printed: Jul. 28, 2004).

Schessel, Eli S. et al., "External Constant Tension Expansion of Soft Tissue for the Treatment of Ulceration of the Foot and Ankle," Journal of Foot & Ankle Surgery, vol. 39, No. 5, pp. 321-328, Sep./Oct. 2000.

Galil, K. et al., "Effect ofN-Butyl-2-Cyanoacrylate (Histoacryl Blue) on the Healing of Skin Wounds," J. Canad. Dent. Assn., No. 7, pp. 565-569 (1984).

Gibson, T. et al., "Directional Variation in Extensibility of Human Skin in Vivo," J. Biomechanics, vol. 2, pp. 201-204 (1969).

Gibson, T. et al., "The Mobile Micro-Architecture of Dermal Collagen," Brit. J. Surg . . . , vol. 52, No. 10, pp. 764-170 (Oct. 1965).

Hirshowitz, B. et al., "A Skin-Stretching Device for the Harnessing of the Viscoelastic Properties of Skin," Plastic and Reconstructive Surgery, vol. 92 No. 2, pp. 260-270 (Aug. 1993).

Liang, M. et al., "Presuturing—A New Technique for Closing Large Skin Defects: Clinical and Experimental Studies," Plastic and Reconstructive Surgery, vol. 81, No. 5, pp. 694-702 (May 1988).

Mustoe, T. et al., "Physical, Biomechanical, Histologic, and Biochemical Effects of Rapid versus Conventional Tissue Expansion," Plastic and Reconstructive Surgery, vol. 83, No. 4, pp. 687-691 (Apr. 1989).

Radovan, C., "Tissue Expansion in Soft-Tissue Reconstruction," Plastic and Reconstructive Surgery, vol. 74, No. I, pp. 482-490 (Oct. 1984).

Stark, H. et al., "Directional Variations in the Extensibility of Human Skin," British Journal of Plastic Surgery, vol. 30, pp. 105-114 (1977).

Prosecution History of U.S. Appl. No. 12/750,353 (Restriction Requirement dated Sep. 23, 201 O; Response dated Oct. 22, 201 O; Office Action dated Nov. 26, 2010; Response dated May 26, 2011).

* cited by examiner

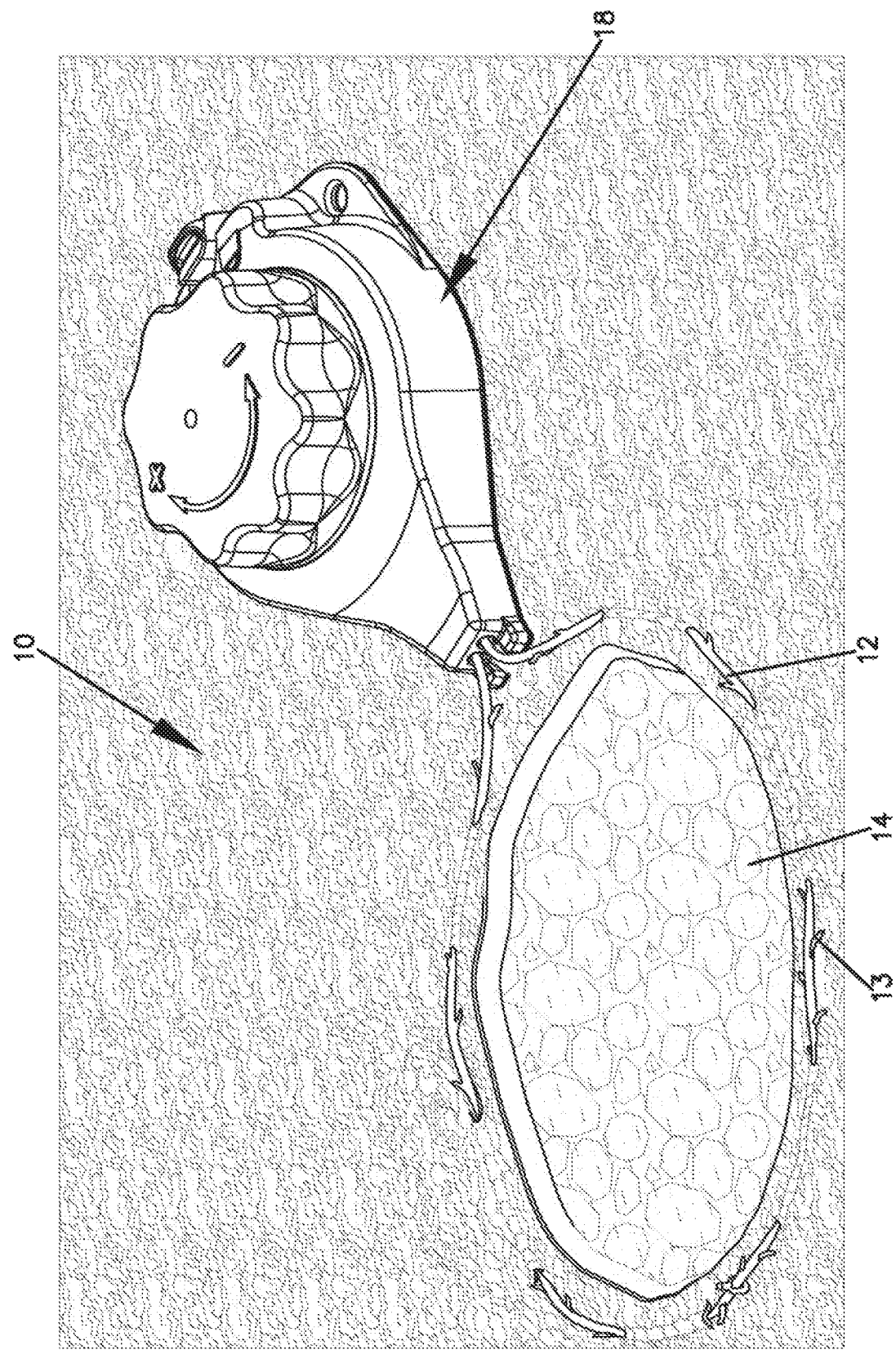

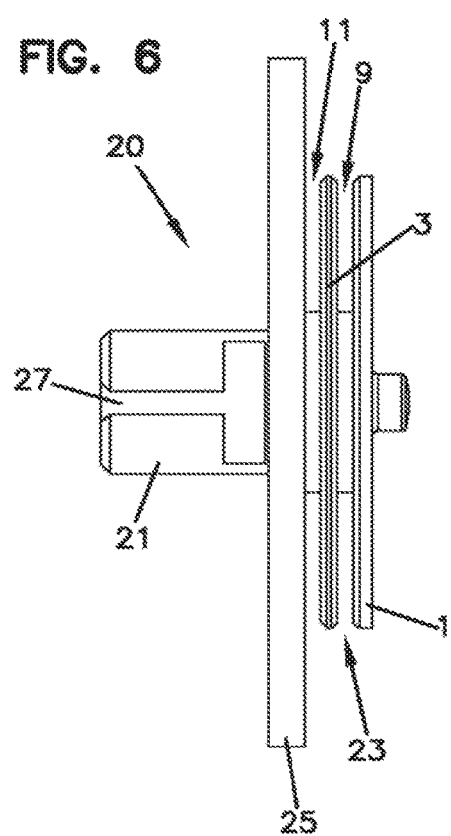
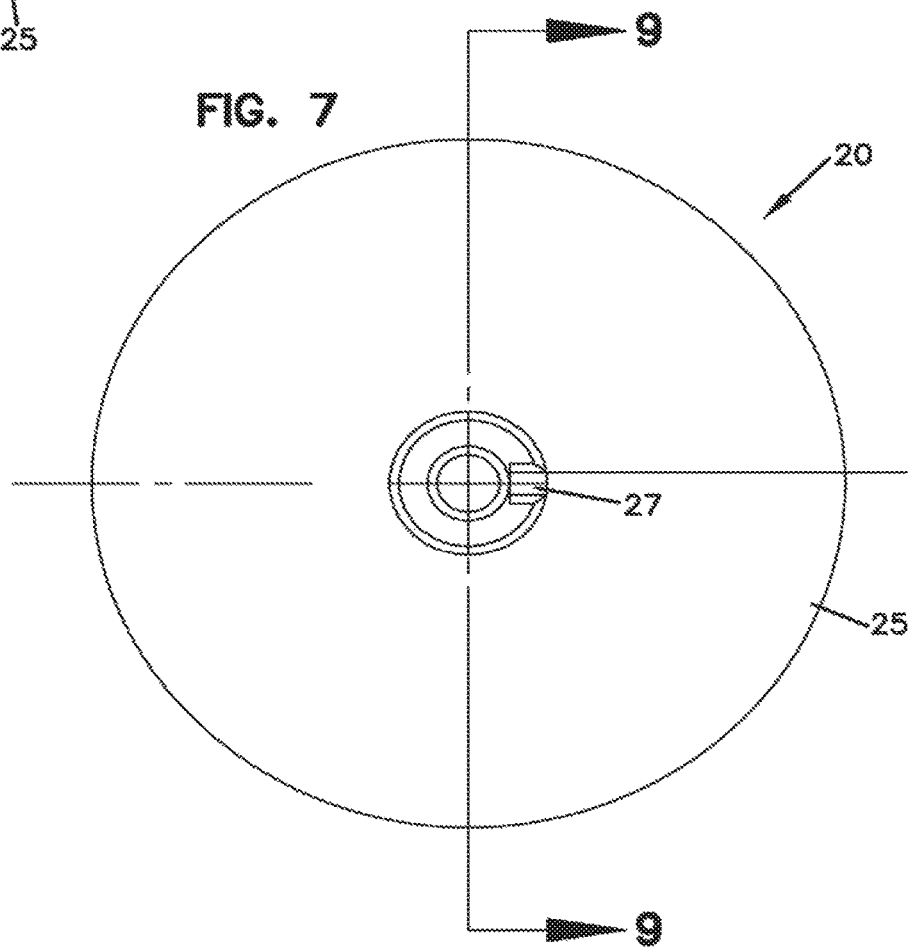

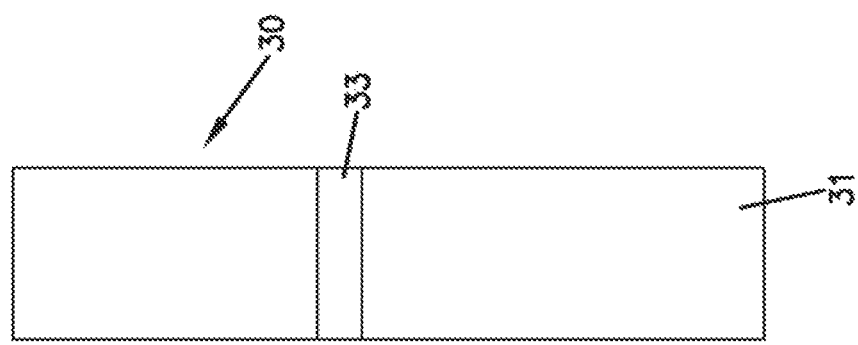
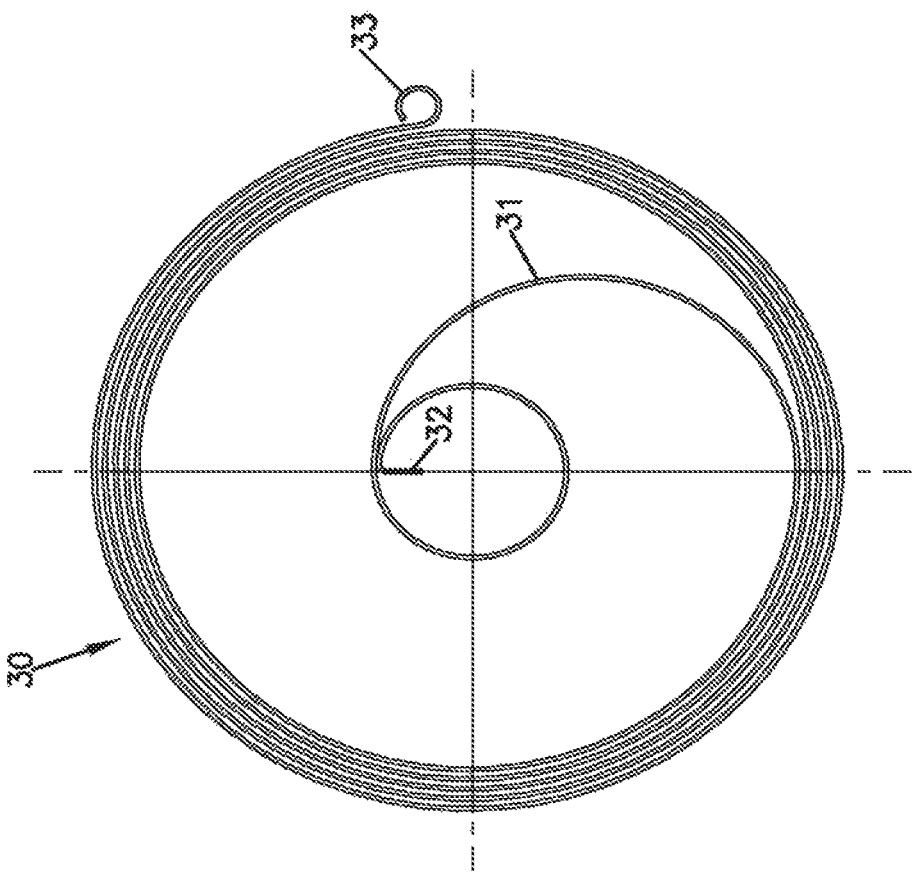

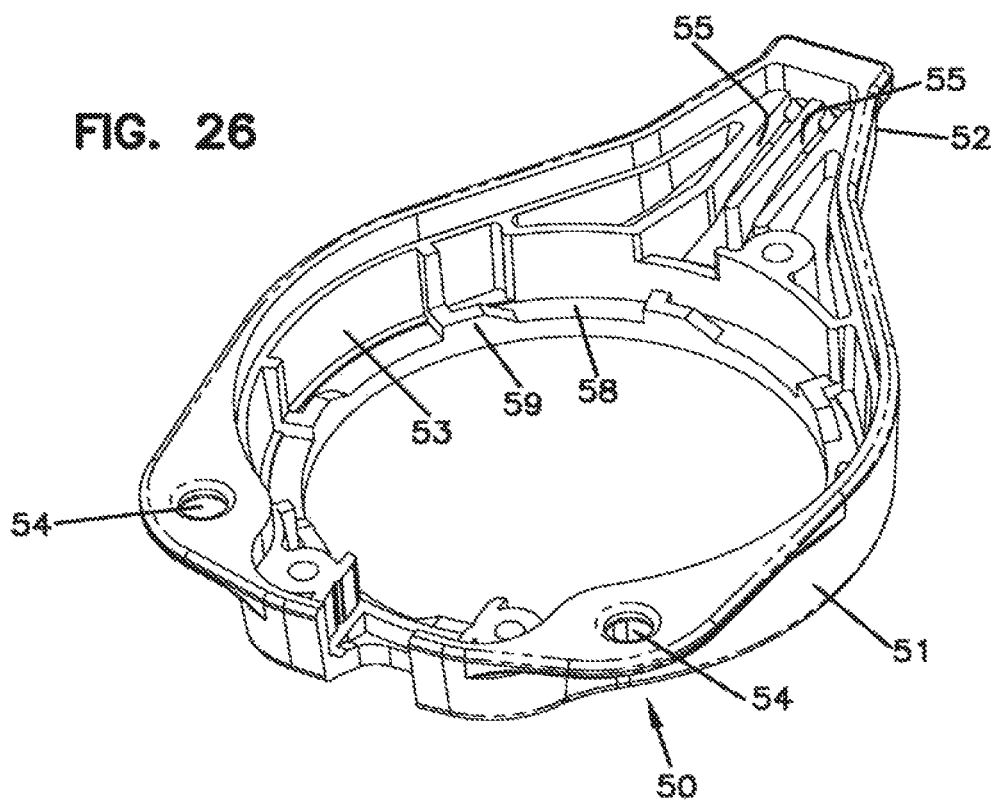
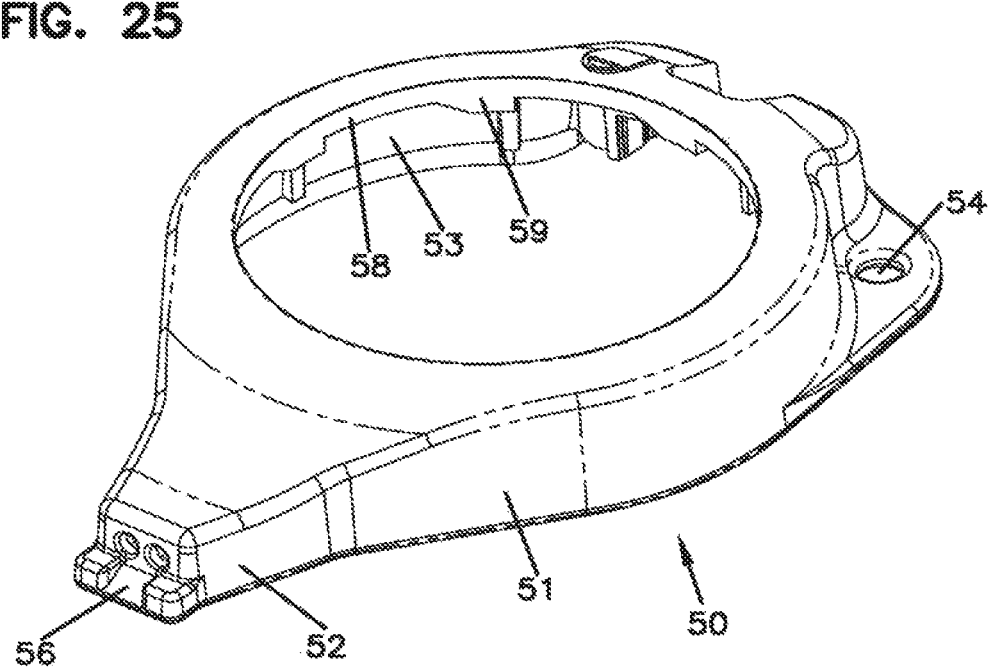

WOUND CLOSURE SYSTEM

CROSS REFERENCE TO RELATED APPLICATIONS

This application is a continuation of application Ser. No. 12/839,156, filed on Jul. 19, 2010, entitled "WOUND CLOSURE SYSTEM", which is incorporated herein by reference in its entirety.

TECHNICAL FIELD

The principles disclosed herein relate generally to wound closure by facilitating stretching of body tissue. More specifically, the disclosure relates to a system and method of facilitating stretching the body tissue adjacent a wound by use of continuous or dynamic force.

BACKGROUND

Surgical procedures such as tumor removal or fasciotomies can result in large skin wounds. Chronic wounds such as diabetic ulcers frequently do not heal. Techniques have been developed to facilitate the wound closure of large skin defects and chronic wounds.

Common methods for closure of wounds and skin defects include split thickness skin grafting, flap closure and gradual closure utilizing tissue expansion. A split thickness skin graft involves removing a partial layer of skin from a donor site, usually an upper leg or thigh, and leaving the dermis at the donor site to re-epithelialize. In this manner, a viable skin repair patch can be transferred or grafted to cover the wound area. The graft is often meshed, (which involves cutting the skin in a series of rows of offset longitudinal interdigitating cuts) allowing the graft to stretch to cover an area two or three times greater than the wound, as well as provide wound drainage while healing. Normal biological function of the skin heals the cuts after the graft has been accepted. A meshed graft of this type requires a smaller donor area than a conventional non-meshed or full thickness skin graft. Flap closure involves transferring skin from an adjacent region to the wound. This technique is only effective in anatomical regions that are amenable to transfer of adjacent skin. It is also a more complex surgical procedure involving increased surgical costs and risks. Both of these methods do not provide optimal cosmesis or quality of skin cover. Other disadvantages of these methods include pain at the donor site, creation of an additional disfiguring wound, and complications associated with incomplete "take" of the graft. In addition, skin grafting often requires immobilization of the limb, which increases the likelihood of contractures. The additional operation and prolongation of hospital stay is an additional economic burden.

Gradual, or progressive, closure is another method of wound closure. This technique may involve suturing vessel loops to the wound edge and drawing them together with large sutures in a fashion similar to lacing a shoe. In addition, the wound edges may be progressively approximated with suture or sterile paper tape. The advantages of this gradual, or progressive, technique are numerous: no donor site is required for harvest of a graft limb mobility is maintained; superior cosmetic result, more durable skin coverage, better protection because skin is full thickness, and maintenance of normal skin sensation may all be achieved.

Existing devices for effecting a gradual closure, however, have many disadvantages. Current methods and devices rely on static or elastic ribbon or suture material which must be repeatedly readjusted in order to draw wound edges together because a relatively small skin movement substantially eliminates much of the closure force. Even with constant readjustment, maintenance of near constant tension over time is difficult, if not impossible, to achieve. Since widely used existing closure techniques involve use of relatively inelastic materials such as sutures or surgical tape, a substantial amount of tension is put on the wound edges during periodic adjustment to obtain the necessary closure force. Excessive tension may cut the skin or cause necrosis due to point loading of the tissue.

What is needed in the art is a gradual wound closure technique that is self-regulating and self-adjusting and uses continuous or dynamic tension to draw the wound edges together, without the need for constant readjustment involved with the static systems.

SUMMARY

The principles disclosed herein relate to wound closure by facilitating stretching of body tissue. The disclosure relates to a system and method of facilitating stretching/expanding the body tissue adjacent a wound by use of dynamic or continuous force.

According to the present disclosure, the term "body tissue" may refer to human or animal tissue and may include internal and external tissue such as skin tissue (the epidermis and the dermis), subcutaneous tissue (the hypodermis), fascia tissue, organ tissue, etc.

The disclosure is directed to a wound closure system including components adapted to apply a dynamic or continuous tension force on a suture line that is sutured to body tissue surrounding a wound. The dynamic tension force draws the suture line toward the wound closure system facilitating stretching of the body tissue over the wound area.

In one particular aspect, the disclosure is directed to a wound closure system comprising a biasing member that applies a dynamic or continuous force to a suture line that is sutured to body tissue surrounding a wound, wherein the suture line includes a plurality of barbs configured to grab the body tissue. According to one embodiment, the barbed suture line extends around substantially the entire periphery of the wound and application of tension to the suture line draws and stretches the body tissue toward the wound. According to another embodiment, the suture line can also be sutured to the body tissue surrounding the wound in a manner so as to extend across the wound, i.e., in a "shoelace" configuration in use of the wound closure system.

In another particular aspect, the biasing member that provides tension on the barbed suture line may be included as part of a separate tensioning apparatus that may be fixedly attached near the vicinity of the wound area. In other embodiments, the tensioning apparatus may be attached further away from the wound area, with the dynamic tension force being directed to the wound area.

In another particular aspect, instead of including a separate tensioning apparatus, the wound closure system may utilize a line that is connected to the barbed suture line or the barbed suture line itself that includes elastic material to provide the dynamic tension on the body tissue surrounding the wound. Also, an elastic line or elastic suture line can be used in combination with a separate tensioning apparatus.

In yet another particular aspect, the disclosure is directed to a method of closing a wound, the method comprising the steps of suturing a barbed suture line to body tissue surrounding a wound and applying a dynamic or continuous tension force on the suture line to draw and stretch the body tissue toward the wound.

In yet another particular aspect, the disclosure is directed to a wound closure kit comprising a barbed suture line for attachment to body tissue surrounding a wound and a biasing member adapted to provide continuous or dynamic tension on the line for stretching body tissue.

BRIEF DESCRIPTION OF THE DRAWINGS

The accompanying drawings, which are incorporated in and constitute a part of the description, illustrate several aspects of the disclosure and together with the detailed description, serve to explain the principles of the disclosure. A brief description of the drawings is as follows:

FIG. 2 illustrates the wound closure system of FIG. 1 in operation adjacent a wound area;

FIG. 6 is a side elevation view of a spool of the tensioning apparatus of FIG. 3;

FIG. 7 is a top plan view of the spool of FIG. 6;

FIG. 18 is a top plan view of the biasing member of FIG. 17;

FIG. 19 is a side elevation view of the biasing member of FIG. 17;

FIG. 25 is a top perspective view of a cover of the tensioning apparatus of FIG. 3;

FIG. 26 is a bottom perspective view of the cover of FIG. 25;

DETAILED DESCRIPTION

The inventive aspects of the disclosure will now be described by reference to the several drawing figures.

A. Wound Closure System

Figure 1:
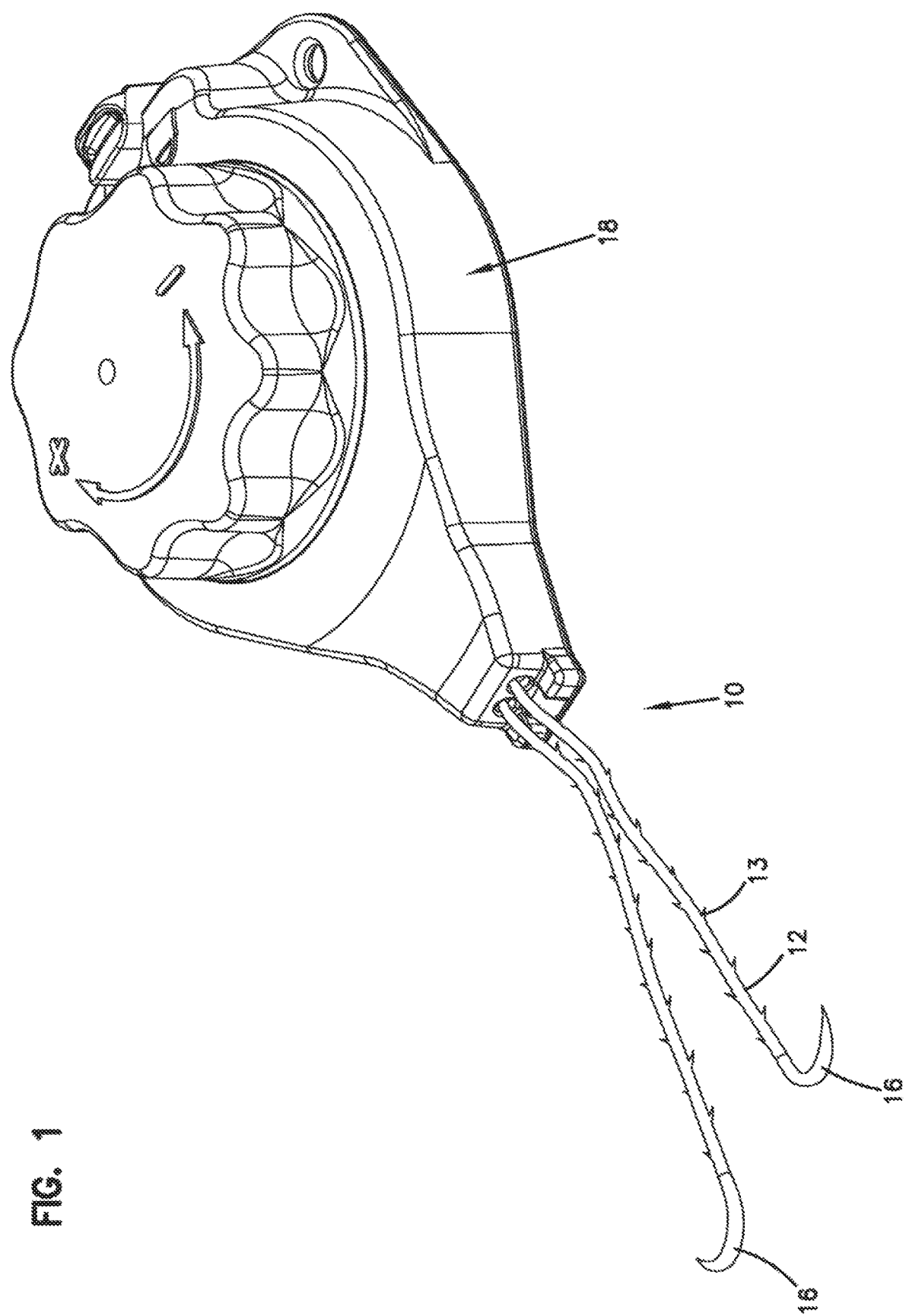
FIG. 1 is a perspective view of a wound closure system in accordance with the principles of the present disclosure.

FIGS. 1 and 2 illustrate one embodiment of a wound closure system 10 having features that are examples of inventive aspects disclosed herein. The wound closure system 10 includes a suture line 12 having a plurality of barbs 13 distributed around the circumference of the suture line 12. The barbed suture line 12 is configured to be sutured to body tissue surrounding a wound 14, as shown in FIG. 2. The barbed suture line 12 may include needles 16 at the ends thereof to facilitate suturing the line 12 to body tissue. As shown in FIG. 2, once the line 12 has been sutured around the wound area 14, the needles 16 may be removed and the ends tied together to form a closed loop around the wound area 14.

The wound closure system 10 illustrated in FIGS. 1 and 2 includes a tensioning apparatus 18 configured to apply dynamic or continuous tension to the barbed suture line 12 after the line 12 has been sutured into body tissue surrounding the wound 14. When tension is applied to the barbed suture 12, the body tissue is stretched toward or over the wound area 14 to decrease the size of the open wound area 14.

According to one embodiment of the suture line of the wound closure system 18, the barbs 13 of the suture line 12 may be unidirectional such that all of the barbs 13 extend out at an acute angle along the same direction with respect to the longitudinal axis of the suture line 12.

As will be discussed in further detail below, it is also contemplated that the suture line 12 could be provided with two sections of barbs 13, wherein all the barbs 13 in the first section extend out at an acute angle in a first direction and all the barbs 13 in the second section extend out at an acute angle in a second opposite direction. Such suture lines can be used, for example, when body tissue on opposing sides of a wound 14 are sutured starting from the same point going to the opposite end of the wound 14. As shown in FIG. 1, if the depicted barbed suture line 12 extending out of the tensioning apparatus 18 was a single line, then the line might include such a two-section barb distribution. However, the embodiment shown in FIG. 1 could be an example that includes two separate suture lines 12 that are attached to a spool structure 20 within the tensioning apparatus 18 and wound separately within the tensioning apparatus 18 as will be discussed in further detail below.

The barbs 13 of the barbed suture 12 may be flexible such that, when suturing, they elastically flex inwardly toward the line surface to facilitate passing through body tissue. When a barb 13 passes through the body tissue and comes out the other side of the body tissue, the barb 13 flexes again outwardly from the suture line surface to provide a catch and grabs the body tissue if the suture 12 is pulled in the opposite direction. In this manner, the barbed suture 12 can be sutured through the body tissue as in a conventional suture, however, preventing any back-up of the suture once passed through body tissue.

It should be noted that the wound closure system 10 can be used to apply a tension force on the suture line 12 in either direction with respect to the barbs 13. For example, if the tension is applied with the direction of the barbs 13, the barbed suture 12 operates in a similar manner to a conventional suture and slides through the body tissue to pull the sides of the body tissue toward or over the open wound area 14. However, as noted above, the barbs 13 still play a role during the initial suturing of the body tissue by preventing back-up of the suture line 12. If the wound closure system 10 is used such that tension is applied against the direction of the barbs 13, the body tissue is stretched toward or over the open wound area 14 by the grabbing action of the barbs 13.

Figure 40:
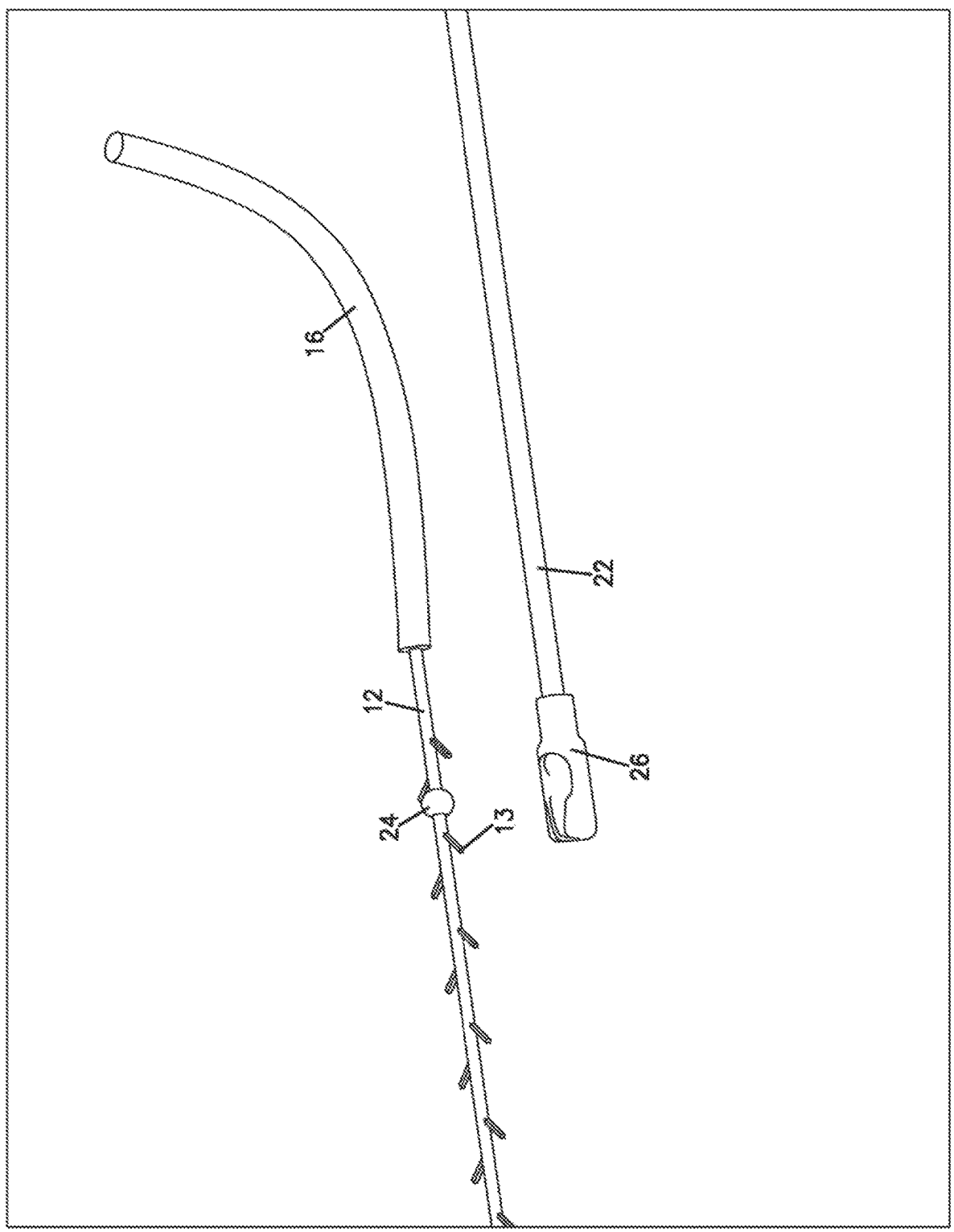
FIGS. 40-42 illustrate one exemplary method of attachment for attaching a barbed suture of the wound closure system of FIGS. 1-2 to a tension line wrapped around the spool of the tensioning apparatus of FIG. 3.
Figure 41:
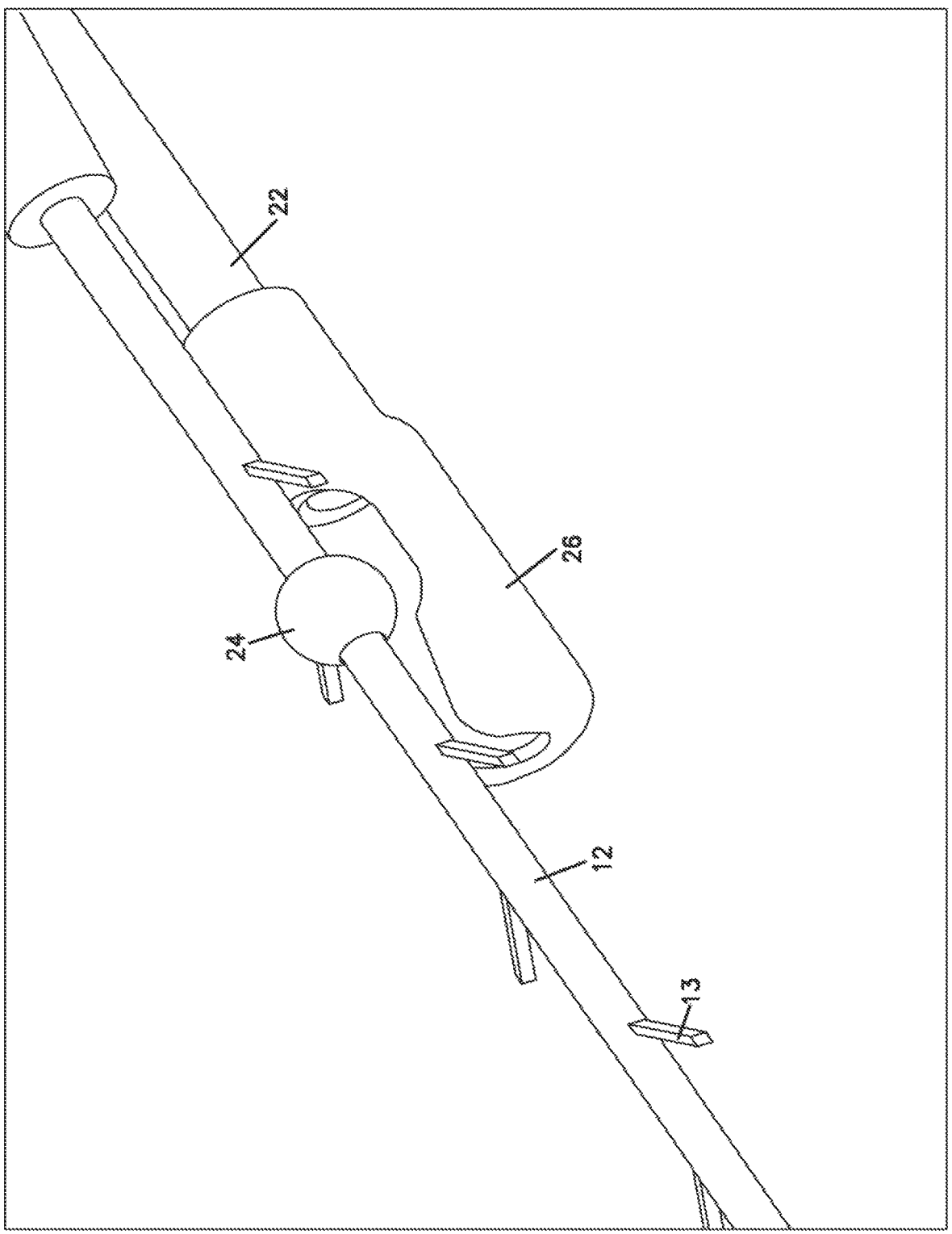
Figure 42:
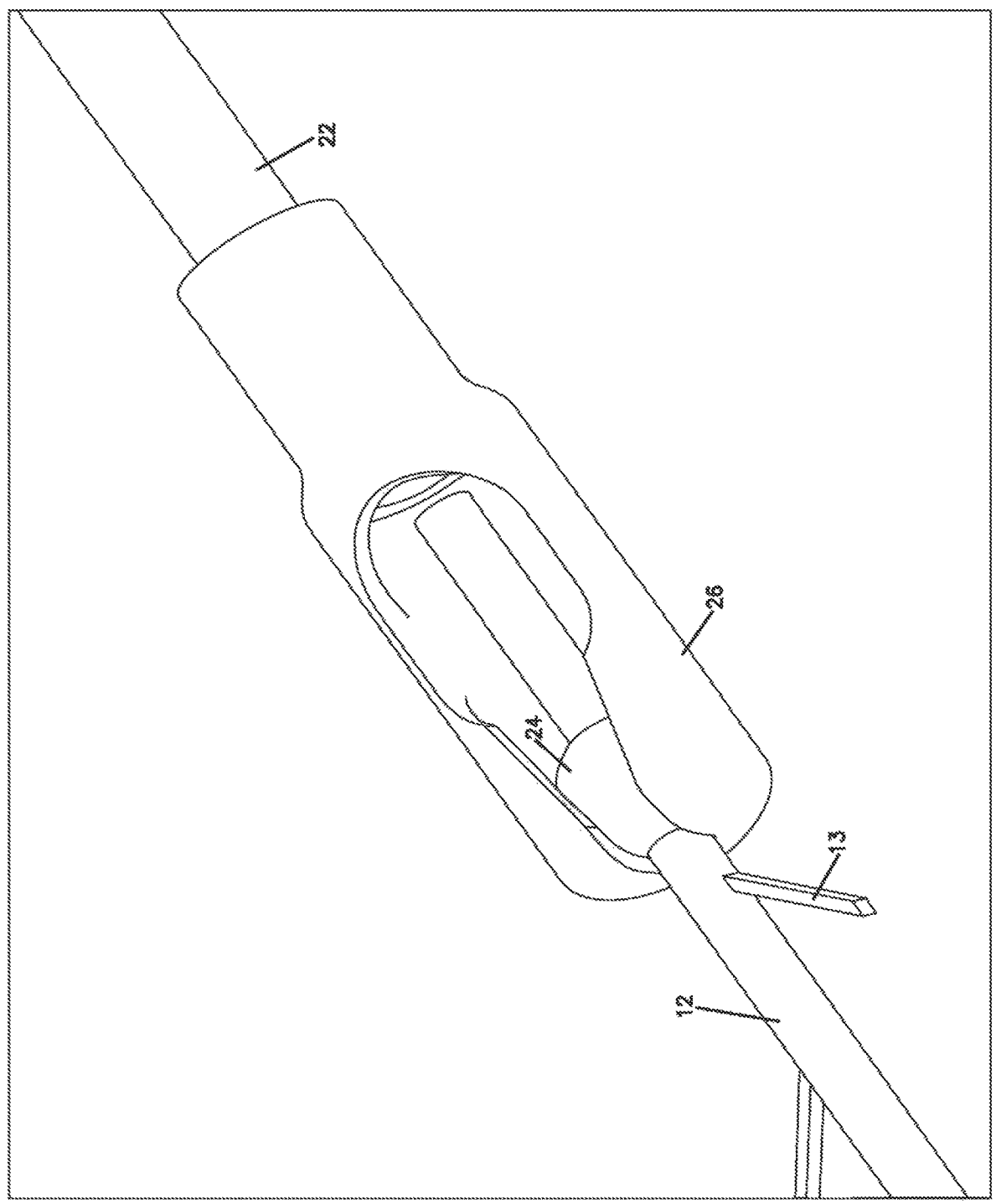

According to one embodiment, the tensioning apparatus 18 of the wound closure system 10 may also include a separate line 22 that is wound within the tensioning apparatus 18 and that is adapted to be attached to the barbed suture line 12. This line 22 may be referred to as a tension line 22 within the present disclosure. One example method of attaching the barbed suture line 12 to a tension line 22 that is already wound within the tensioning apparatus 18 is shown in FIGS. 40-42. As shown in FIGS. 40-42, according to one embodiment, the barbed suture line 12 may include a crimp structure 24 at one of the ends of the barbed suture line 12. The end that includes the crimp structure 24 could be the end with the needle 16 or the opposite end. The crimp structure 24 is inserted into a receiver structure 26 attached to one of the ends of the tension line 22 that is wound within the tensioning apparatus 18. Further details of such an attachment system will be discussed below. Other methods of attachment, including tying a knot between the barbed suture line 12 and the tension line 22, may be used in attaching the barbed suture line 12 to a separate tension line 22 wrapped around the spool 20 of the tensioning apparatus 18 of FIGS. 3-5.

Although the embodiment of the wound closure system 10 illustrated in FIGS. 1-2 is depicted as including a separate tensioning apparatus 18, the wound closure system may instead simply utilize an elastic line that is connected to the barbed suture line 12. In other embodiments, the barbed suture line 12 may include elastic properties and may be used as the elastic line itself that provides a biasing force to apply the dynamic tension on the body tissue surrounding the wound 14. An elastic line or elastic suture line can also be used in combination with a separate tensioning apparatus such as the tensioning apparatus 18 shown in FIGS. 1-5.

With the use of a separate tensioning apparatus 18, an inelastic line 22 connected to a barbed suture line 12 or simply an inelastic barbed suture line 12 can be utilized to draw the body tissue toward the wound 14 since the tensioning apparatus 18 provides the biasing mechanism adapted to provide the dynamic or continuous force needed for wound closure.

According to one embodiment, tensioning apparatus 18 includes a biasing member 30 (shown in FIGS. 3 and 17-19) mounted within the tensioning apparatus 18 to provide the dynamic or continuous tension force on barbed suture line 12. As the body tissue stretches and grows over the wound 14, the body tissue moves toward the wound area, reducing the size of the open wound area 14 and at the same time reducing the tension on the barbed suture line 12, creating "slack" on the line 12. Biasing member 30 provides tension to take up this slack on the line 12. Although depicted as a coiled spring in FIGS. 3 and 17-19, the biasing member 30 may include other structures. The biasing member 30 may be a constant-force spring designed to provide a constant level of tension on the line 12, 22 when it is in a loaded state. The biasing member 30 may alternatively be a nonconstant-force spring designed to provide varying amounts of force on the line 12, 22 depending upon how tightly it is wound. As one skilled in the art will appreciate, the force application characteristics of such springs depend upon factors such as the mechanical properties of the springs.

In certain embodiments, the tension force that is applied to the barbed suture 12 is usually at least 1 oz. and usually no greater than sixty-four oz., commonly between thirty and fifty oz.

If a separate tensioning apparatus 18 is used in the wound closure system, that tensioning apparatus 18 may be secured to a patient by mechanical attachment means such as by adhesives, by suturing, or by other methods as will be discussed in further detail below. The tensioning apparatus 18 can be located proximate to the wound area 14 or may be provided at a distant location remote from the patient's body, with the tension force still being directed to the wound area 14.

Depending upon the arrangement of the wound closure system (e.g., with the use of multiple tensioning apparatuses) and the barbed suture line with respect to the wound, the wound closure system 10 can be used to close virtually any sized wound.

B. Tensioning Apparatus

Figure 3:
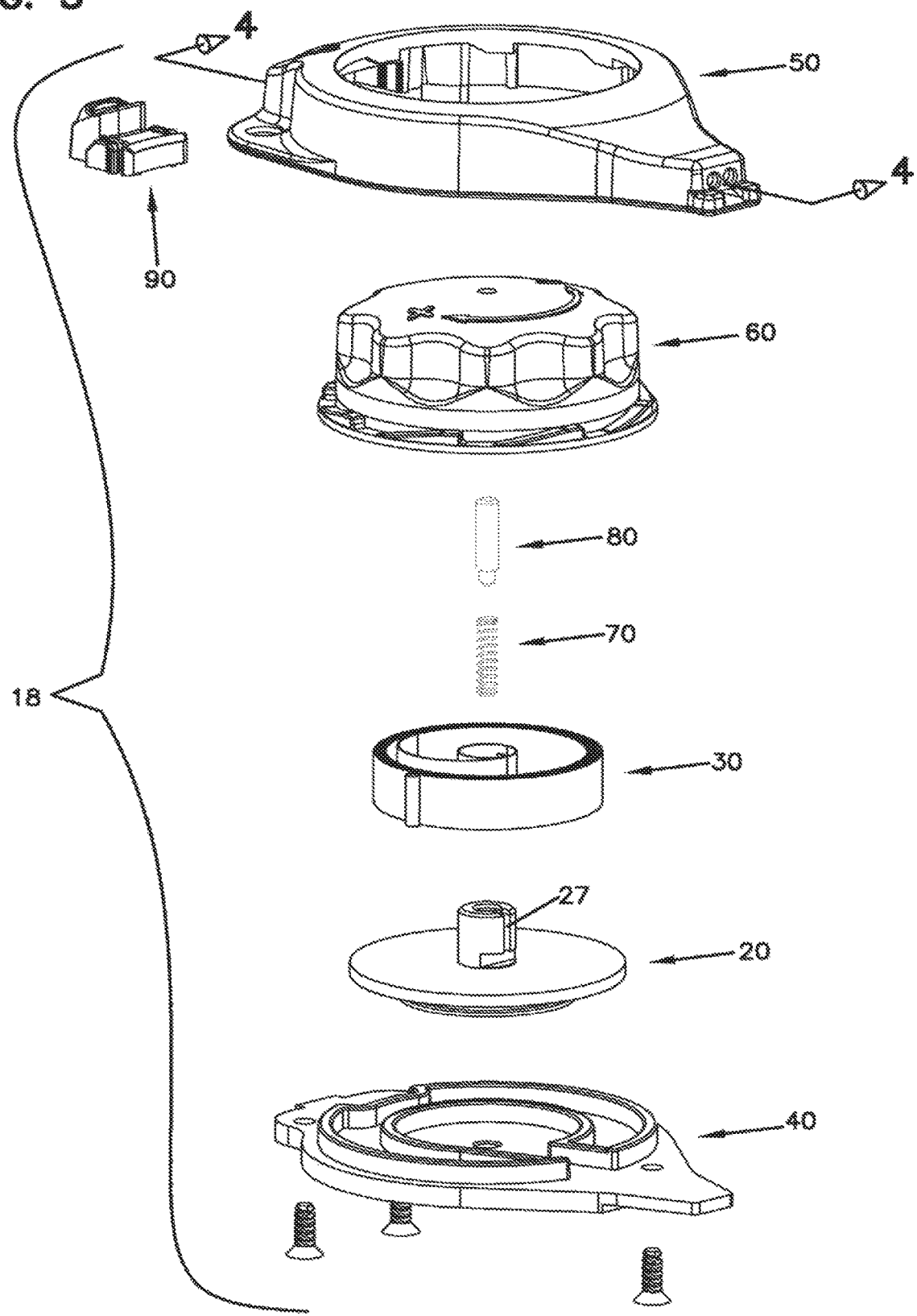
FIG. 3 is an exploded perspective view of a tensioning apparatus of the wound closure system of FIG. 1.
Figure 4:
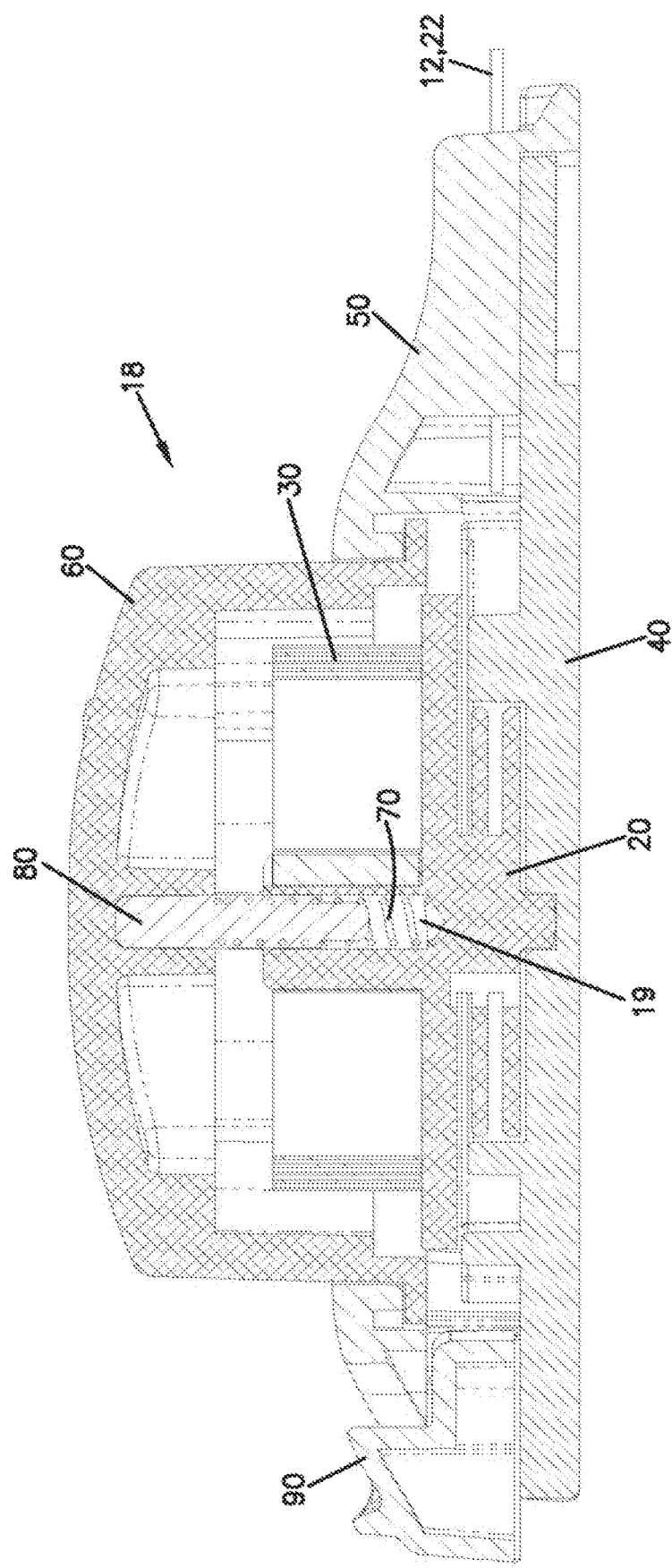
FIG. 4 is a cross-sectional view of the tensioning apparatus of FIG. 3 taken along a line 4-4 of FIG. 3, illustrating a knob of the tensioning apparatus in a fully extended position.
Figure 5:
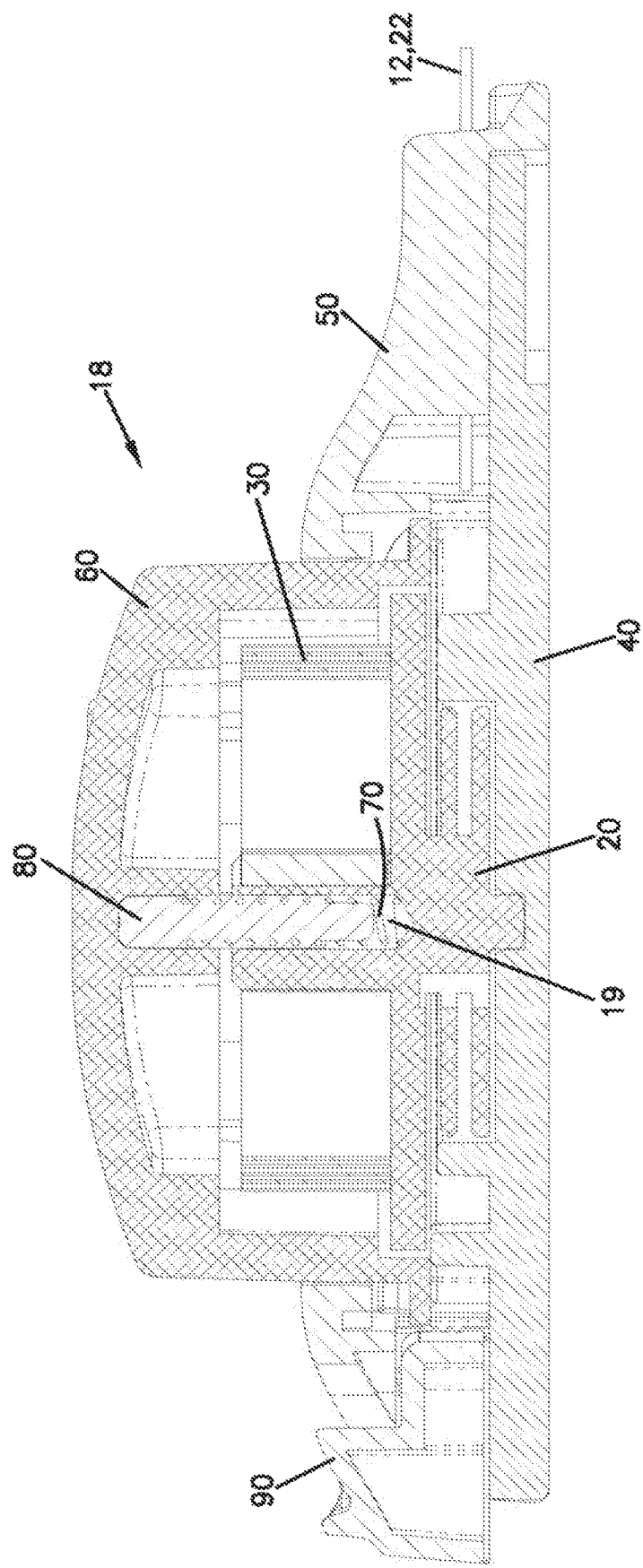
FIG. 5 is a cross-sectional view similar to the view of FIG. 4, illustrating the knob of the tensioning apparatus in a fully depressed position.
Figure 8:
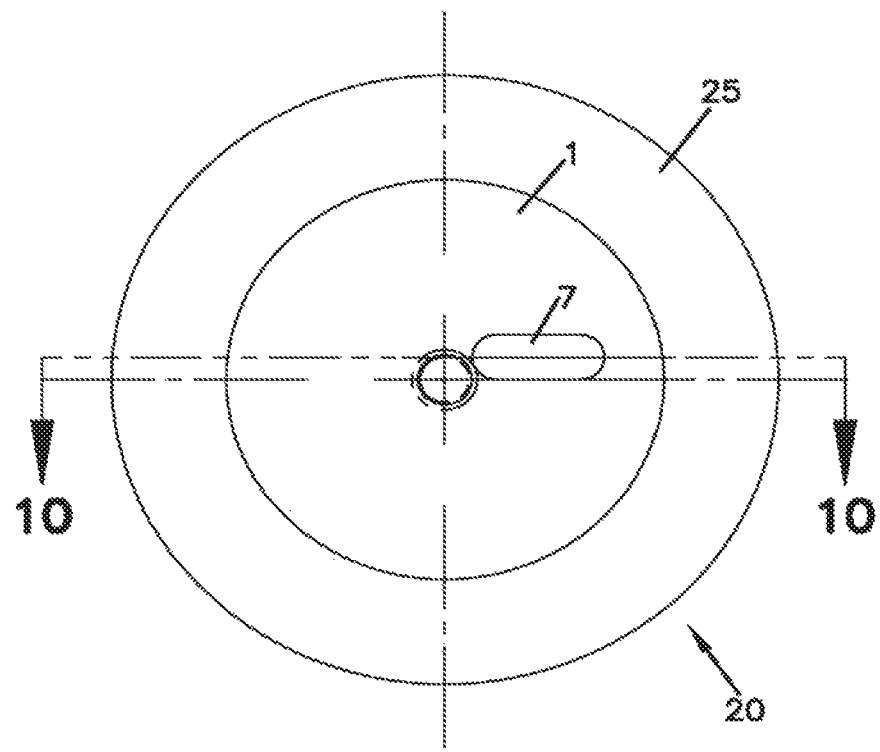
FIG. 8 is a bottom plan view of the spool of FIG. 6.
Figure 9:
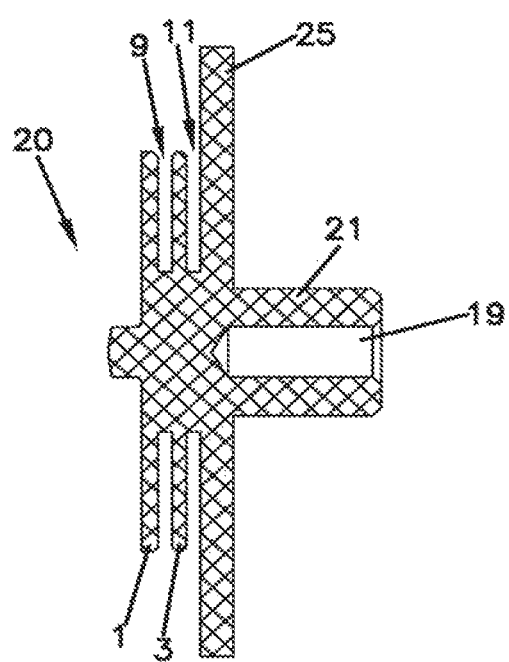
FIG. 9 is a cross-sectional view taken along line 9-9 of FIG. 7.
Figure 10:
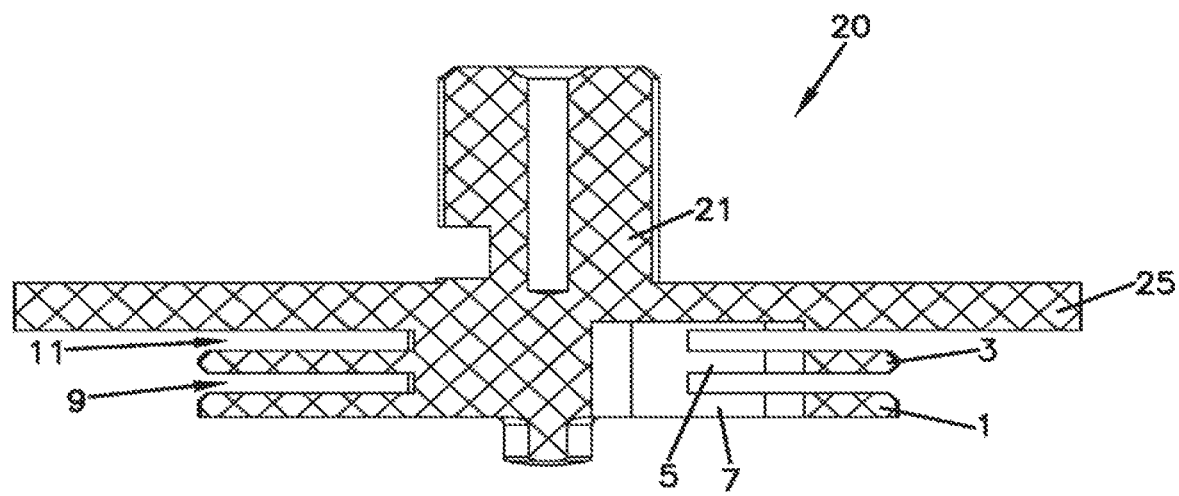
FIG. 10 is a cross-sectional view taken along line 10-10 of FIG. 8.
Figure 11:
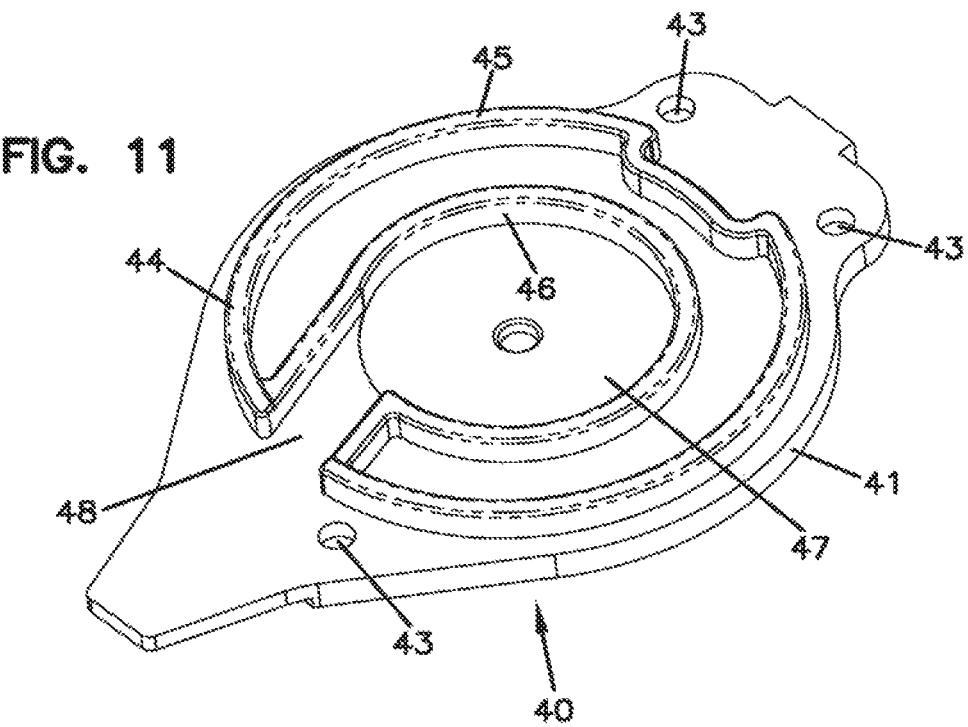
FIG. 11 is a top perspective view of a base of the tensioning apparatus of FIG. 3.

Referring to FIG. 3, an exploded perspective view of the tensioning apparatus 18 of the wound closure system 10 is illustrated therein. The tensioning apparatus 18 of the present disclosure is similar in structure and operation to the tensioning apparatus described in commonly owned U.S. Pat. No. 7,455,681, the entire disclosure of which is hereby incorporated by reference. The tensioning apparatus 18 includes a base 40, a cover 50, a spool 20 that seats on the base 40, the biasing member 30 that is placed around the spool 20, a knob 60 used to wind the biasing member 30 for application of tension, and a linear spring 70 that is placed around a dowel pin 80 that is positioned between the knob 60 and the spool 20. As will be discussed in further detail below, the linear spring 70 provides a biasing force upwardly and allows the knob 60 to be pushed down with respect to the cover 50 to disengage the knob 60 from the cover 50 so that the knob 60 can be turned in a counterclockwise direction to let the line 12 to come out. This may be advantageous during initial set-up or during system removal from the wound area 14. The operation of the linear spring 70, as well as the interaction between the knob 60 and the cover 50 are illustrated in FIGS. 4 and 5.

Referring now to FIGS. 6-10, there is generally illustrated the spool 20 of the tensioning apparatus 18. The spool 20 includes an upper spring mount portion 21, a lower line mount portion 23, and a main plate 25 separating the two portions. In this embodiment, all the portions of the spool 20 are depicted as integrally formed from one unitary piece. However, it will be appreciated that in other embodiments, the spool may be formed from multiple separate pieces that are coupled together.

Figure 37:
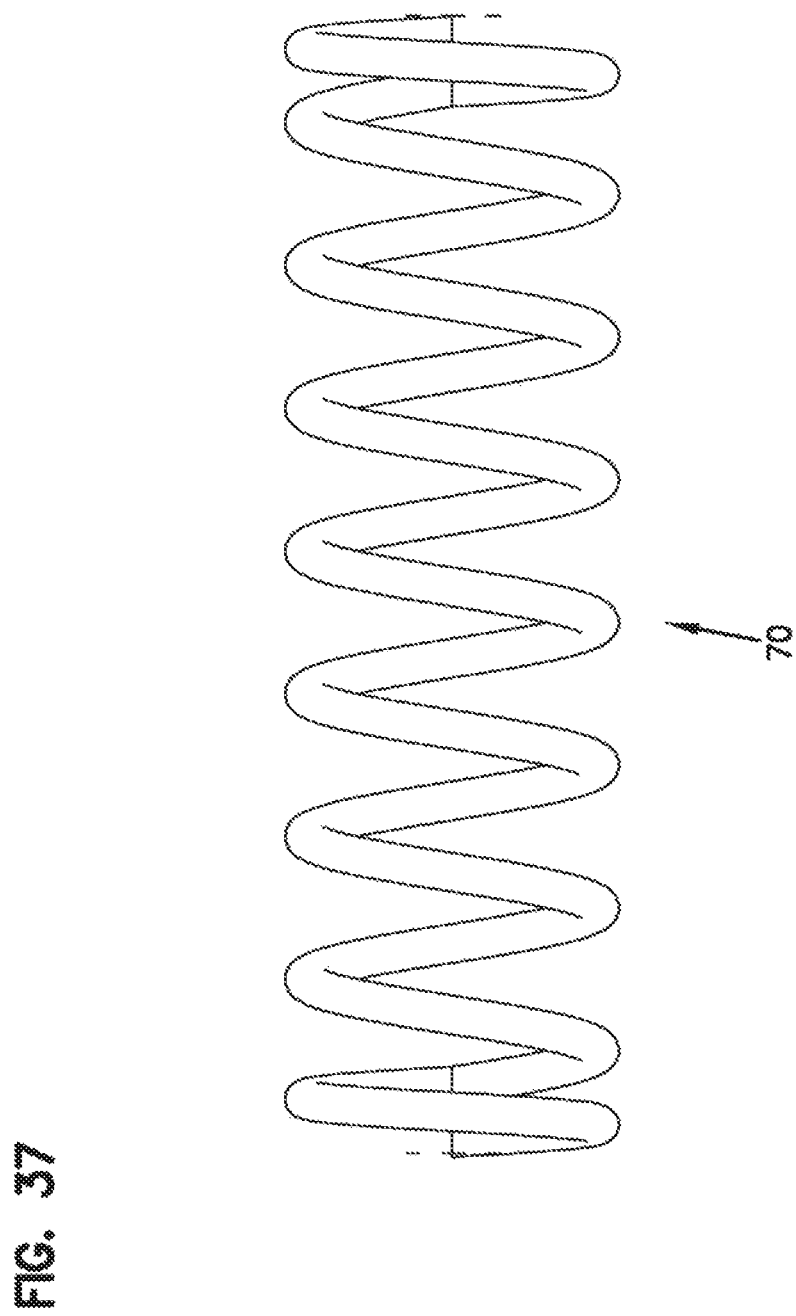
FIG. 37 is a side elevation view of a linear spring configured to be placed around the dowel pin of FIG. 36 between the knob and the spool of the tensioning apparatus of FIG. 3.

The upper spring mount portion 21 has a generally cylindrical shape. The upper mount portion 21 includes a slot 27 adapted to receive one end of the biasing member 30 as will be discussed in further detail below. The upper spring mount portion 21 also includes a well 19 for the placement of the linear spring 70 (see FIGS. 4, 5, and 37). The well 19 is not a throughhole and includes a closed end in the upper spring mount portion 21. When the linear spring 70 is placed within the well 19, a portion of the spring 70 may protrude upwardly out of the well 19.

The lower tension line mount portion 23 defines two winding grooves 9, 11. The lower winding groove 9 is defined between two seat plates, a lower seat plate 1 and an upper seat plate 3. The upper winding groove 11 is defined between the main plate 25 and the upper seat plate 3. The seat plates 1, 3 provide structure for seating the spool 20 into the base 40 of the tensioning apparatus 18. The spool 20 also defines an upper opening 5 going through the upper seat plate 3 and a lower opening 7 going through the lower seat plate 1. The openings 5, 7 in the plates are aligned to define a large opening going through the plates 1, 3. The openings 5, 7 in the seat plates allow a line or lines 12, 22 to be directed between the upper winding groove 11 and the lower winding groove 9 of the spool 20.

The openings 5, 7 can be used such that when a line 12, 22 is inserted through one of the openings 5, 7, a knot may be tied or a crimp tube applied, the knot or the dimension of the crimp tube being large enough that the tied or crimped end of the line 12, 22 will not slip through the opening. Another line or the other end of the same line can be inserted through the opening located in the other seat plate, with a similar knot tied or crimp tube applied. In this manner, a single line or multiple lines 12, 22 can be coupled to the spool 20 ready to be wound. If a single line is used, the two ends of the line are preferably attached to openings in separate seat plates 1, 3 to facilitate winding of the line 12, 22 and keep line 12, 22 untangled during winding. It will be appreciated that there are numerous methods for attaching one or more lines to the spool 20 using the winding grooves 9, 11 and the openings 5, 7 provided in the seat plates 1, 3 of the spool 20.

Referring now to FIGS. 11-16, there is generally illustrated the base 40 of the tensioning apparatus 18. Base 40 includes a generally circular main body portion 41 and an elongated snout portion 42. Disposed around the main body 41 are fastener mounting openings, generally indicated at 43 that may be used to mount the base 40 to cover 50 with fasteners.

The base 40 defines a circumferential wall portion 44 protruding upwardly therefrom. The wall portion 44 defines an exterior wall portion 45 and an interior wall portion 46. The interior wall portion 46 defines an interior cavity 47 shaped to receive the lower tension line mount portion 23 of the spool 20. The wall portion 44 of the base 40 also defines a slot 48 for directing the line 22 outside of the tensioning apparatus 18 and toward the wound 14. Once the line 22 exits the tensioning apparatus 18, the line 22 may be connected to the barbed suture 12, as noted above.

The snout portion 42 of the base 40 is provided with an elongate shape that matches the contour of the cover 50 of the wound closure system 10 for directing the line 22 out of the tensioning apparatus.

Figure 17:
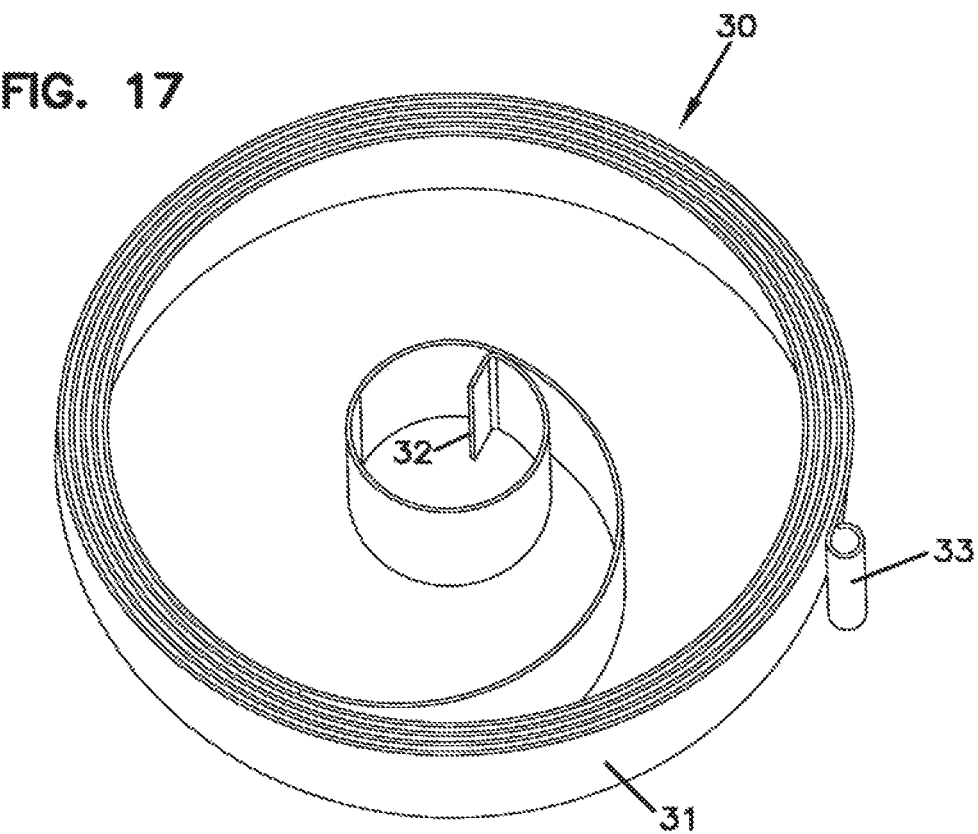
FIG. 17 is a top perspective view of a biasing member of the tensioning apparatus of FIG. 3.
Figure 20:
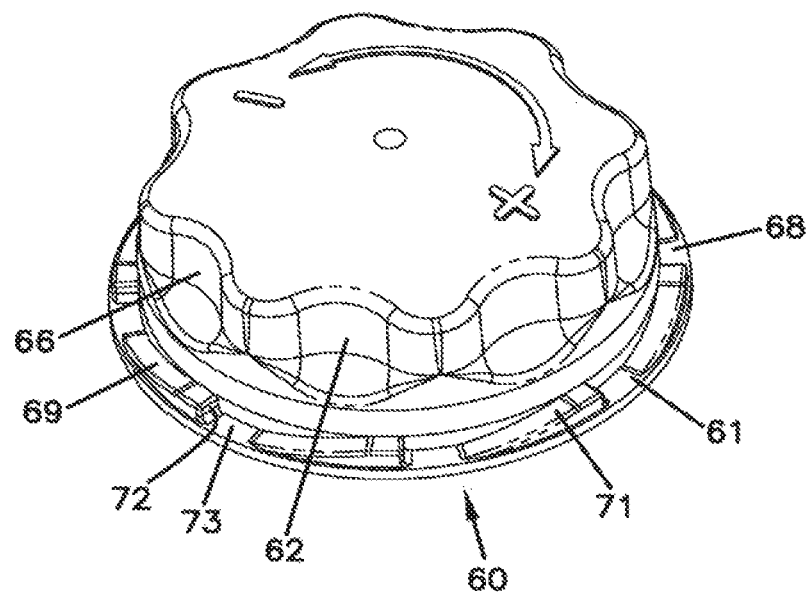
FIG. 20 is a top perspective view of a knob of the tensioning apparatus of FIG. 3.
Figure 21:
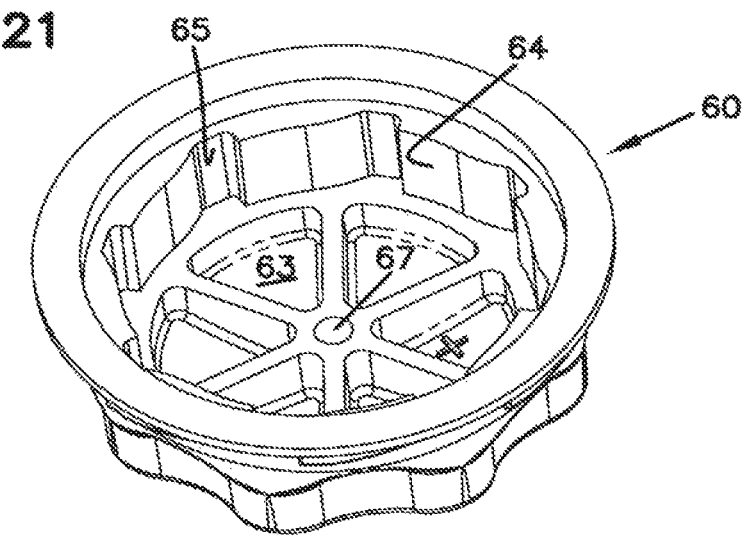
FIG. 21 is a bottom perspective view of the knob of FIG. 20.
Figure 23:
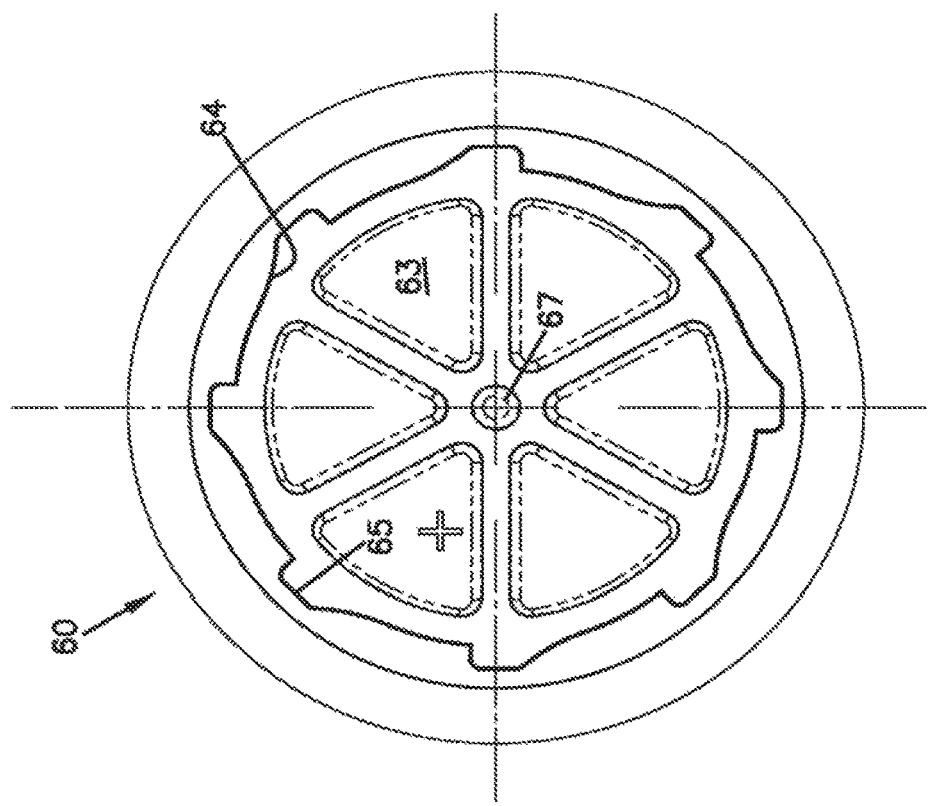
FIG. 23 is a bottom plan view of the knob of FIG. 20.
Figure 22:
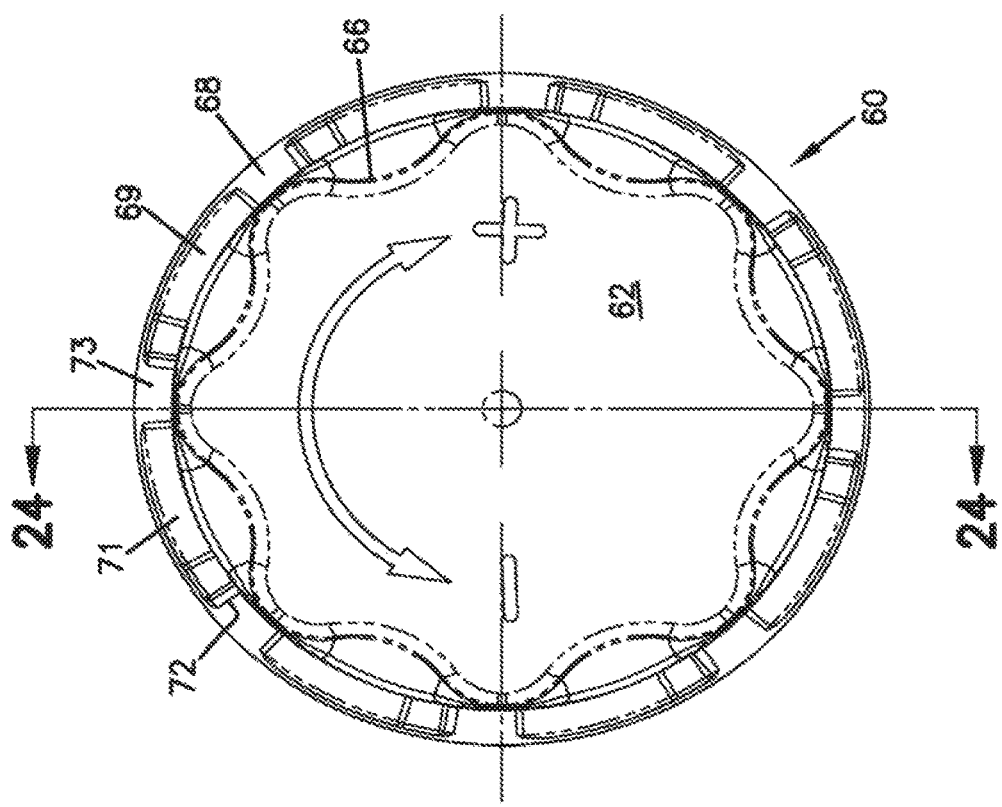
FIG. 22 is a top plan view of the knob of FIG. 20.
Figure 24:
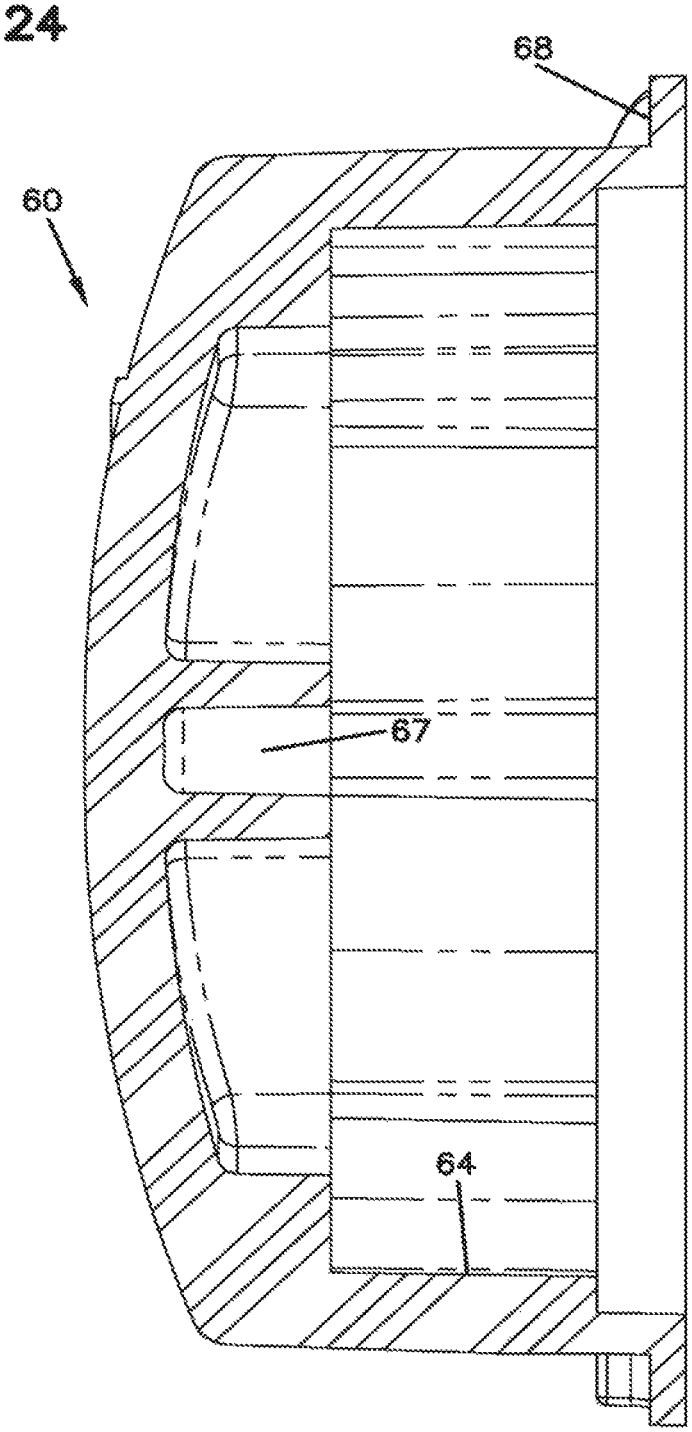
FIG. 24 is a cross-sectional view taken along line 24-24 of FIG. 22.
Figure 27:
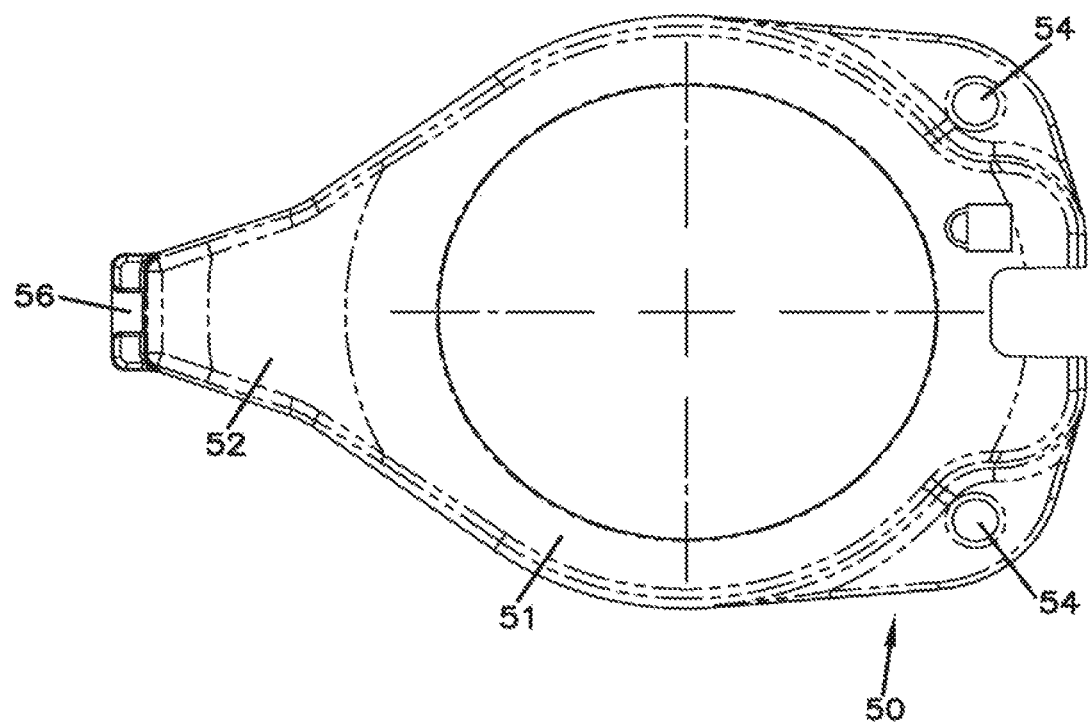
FIG. 27 is a top plan view of the cover of FIG. 25.

Referring now to FIG. 17-19, there is generally illustrated therein the biasing member 30 of the tensioning apparatus 18. The biasing member 30 is depicted as a spring formed from a coiled-up band 31. According to one embodiment, the coiled-up band 31 may be formed from a metal. Other materials are suitable. As discussed previously, the spring 31 can be a constant force spring that provides a constant level of tension regardless of how tight it is wound or it can be a nonconstant-force spring that provides different levels of tension at different degrees of tightening. According to one embodiment, the band 31 is made of type 301 high-yield stainless steel. In certain embodiments, the biasing member 30 can provide a load force of about four lbs. As will be appreciated in the art, the load force of the biasing member 30 can vary depending on certain properties such as the thickness, the diameter, or the material of the band 31.

The band 31 defines an inner end 32 and an outer tab portion 33. The coiled up band 31 is positioned around the upper spring mount portion 21 of the spool 20. When positioned as such, the inner end 32 of the band 31 is placed within the slot 27 defined on the upper spring mount 21 of the spool 20. The outer tab 33 of the band 31 cooperates with the knob 60 of the tensioning apparatus 18 for winding purposes. Winding of the biasing member 30 will be described in detail further below.

Figure 36:
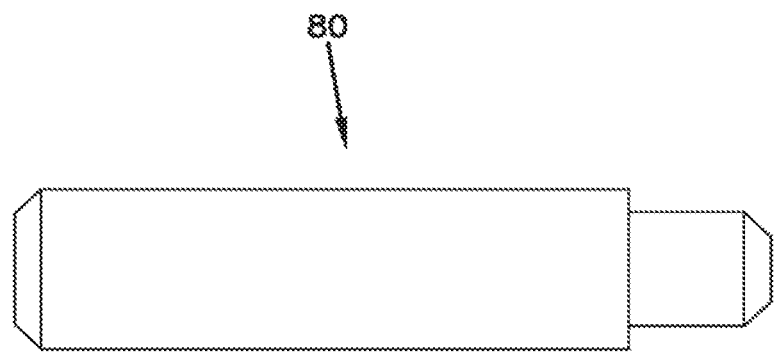
FIG. 36 is a side elevation view of a dowel pin configured to be placed between the knob and the spool of the tensioning apparatus of FIG. 3.

Referring to FIGS. 20-24, there is generally illustrated the knob 60 of the tensioning apparatus 18 that is used to load and unload the biasing member 30. The knob 60 includes a generally cylindrical body 61 with an exterior surface 62 and an interior cavity 63 defined by an interior surface 64. The interior cavity 63 is shaped and sized to tightly receive the biasing member 30. The interior surface 64 includes radially arranged vertical indents 65 that cooperate with the outer tab 33 of the biasing member 30 to wind the biasing member. The interior surface also includes a slot 67 adapted to receive a portion of the dowel pin 80 (seen in FIGS. 4, 5, and 36). As noted previously, the dowel pin 80 is configured to receive the linear spring 70 that is positioned between the knob 60 and the spool 20 and biases the knob 60 upwardly when it is pushed down with respect to the cover 50. See FIGS. 4, 5, 36, and 37.

Still referring to FIGS. 20-24, the exterior surface 62 of the knob 60 defines radially arranged gripping features 66 to facilitate turning the knob during winding. The gripping features 66 are depicted as generally vertical grooves but may be other structures adapted to facilitate the winding process of the biasing member 30.

The exterior surface 62 of the knob 60 also includes a flange 68 with horizontal tabs 69 arranged radially around the circumference of the knob 60. The tabs 69 include ramped surfaces 71 that ramp upwardly in a counterclockwise direction. The tabs 69 define square faces 72 at the end of the ramped surfaces 71. The tabs 69 are spaced and define gaps 73 thereinbetween. The tabs 69 cooperate with the cover 50 of the tensioning apparatus 18 to wind the biasing member 30, to lock the biasing member 30 when it is loaded, and to release the biasing member 30 when desired, as will be described below in further detail.

Referring now to FIGS. 25-30, there is generally illustrated therein the cover 50 of the tensioning apparatus 18. The cover 50 generally includes an interior shape configured to fit on exterior of the base 40. The cover includes a main body portion 51 and an elongate snout portion 52. The main body portion 51 fits over the main body portion 41 of the base 40 and the snout portion 52 fits over the snout portion 42 of the base 40. The cover 50 includes an inner wall 53 that is shaped and sized to snugly fit over the wall portion 44 of the base 40.

Adjacent the rear side, the cover 50 defines holes 54 for suturing the tensioning apparatus 18 to body tissue. As noted previously, although depicted as being adapted for mounting to the body by way of suturing, the cover 50 need not have the suture holes 54 and the tensioning apparatus 18 can be secured to the patient by other methods such as by adhesive, by adhesive tape, by a bandage, by straps, by a wound dressing, etc. As also discussed previously, the tensioning apparatus 18 can also be located at a location outside the patients body if desired, distal to the wound area 14.

The elongate snout portion 52 of the cover 50 defines a pair of channels 55 for guiding the tension line 22 or the barbed suture line 12 toward the wound 14. Either the tension line 22 or the barbed suture line 12 coming out of the tensioning apparatus 18 can, thus, be in line with the rest of the barbed suture line sutured to body tissue around the periphery of the wound 14, as seen in FIG. 2. In this manner, an even distribution of pulling force can be kept on the body tissue around wound 14. Depending on the shape of the wound 14, the snout portion 52 of the cover 50 can be placed at various positions depending on where the force is desired to be concentrated. By providing structural support for the line 12, 22, the snout portion 52 can also allow the tensioning apparatus 18 to be positioned at a remote location from the wound 14. Remote placement of the tensioning apparatus 18 makes it easier to inspect and dress the wound 14.

Figure 38:
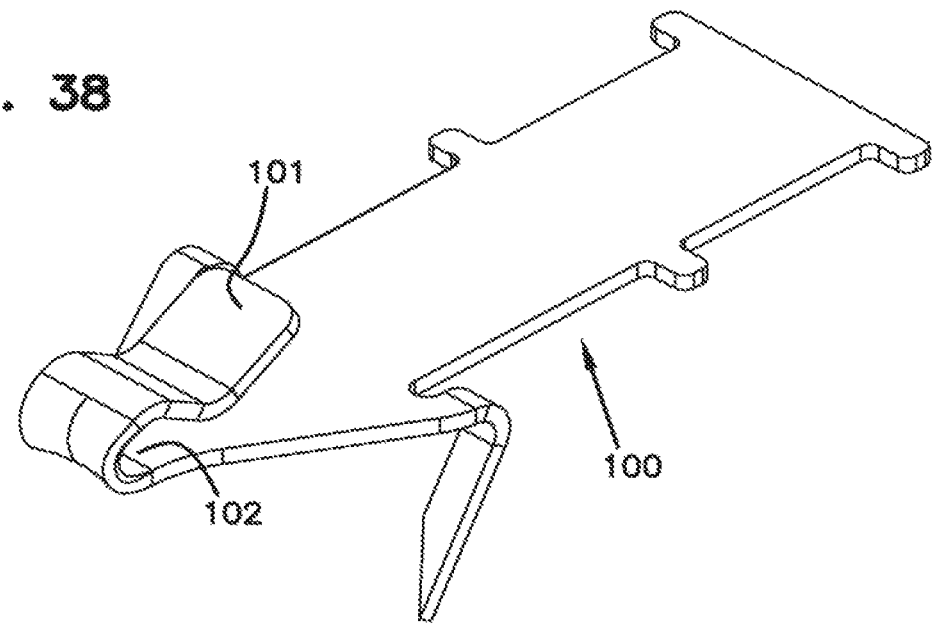
FIG. 38 is a top perspective view of a body anchor suitable for anchoring the tensioning apparatus of FIG. 3 to body tissue around a wound.
Figure 39:
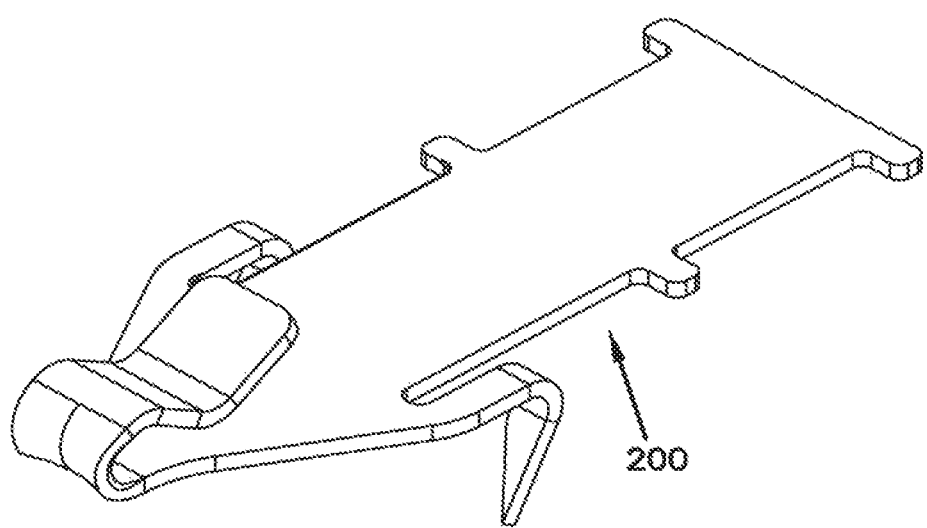
FIG. 39 is a top perspective view of another embodiment of a body anchor suitable for anchoring the tensioning apparatus of FIG. 3 to body tissue around a wound.

The elongate snout portion 52 of the cover 50 can also be used to provide an alternative method of securing the tensioning apparatus to the patient's body. As shown in FIGS. 25, 27, 29, and 30, the front of the snout 52 includes a ramped surface 56. The ramped surface 56 is configured to cooperate with a body anchor 100 (see FIG. 38) that is attached to the body of a patient adjacent the wound 14 as described in U.S. Pat. No. 7,455,681, the entire disclosure of which has been incorporated herein by reference. Please see FIG. 39 for another embodiment of a body anchor 200 suitable for use with the tensioning apparatus 18. As described in U.S. Pat. No. 7,455,681, the tension line tab 101 of an anchor 100 can be used to fixedly mount the cover 50 to the anchor 100. The ramped surface 56 is inserted within the tension line slot 102 defined by the tension line tab 101 of the anchor 100 as the tension line tab 100 abuts against the front of the snout 52. With this feature, the cover 50 can be mounted onto an anchor 100 adjacent the wound 14 and the tensioning apparatus 18 can be allowed to move with the anchor 100 as the body tissue is stretched toward the wound 14. Please refer to FIG. 2 for this type of an attachment method used for the tensioning apparatus 18.

Figure 12:
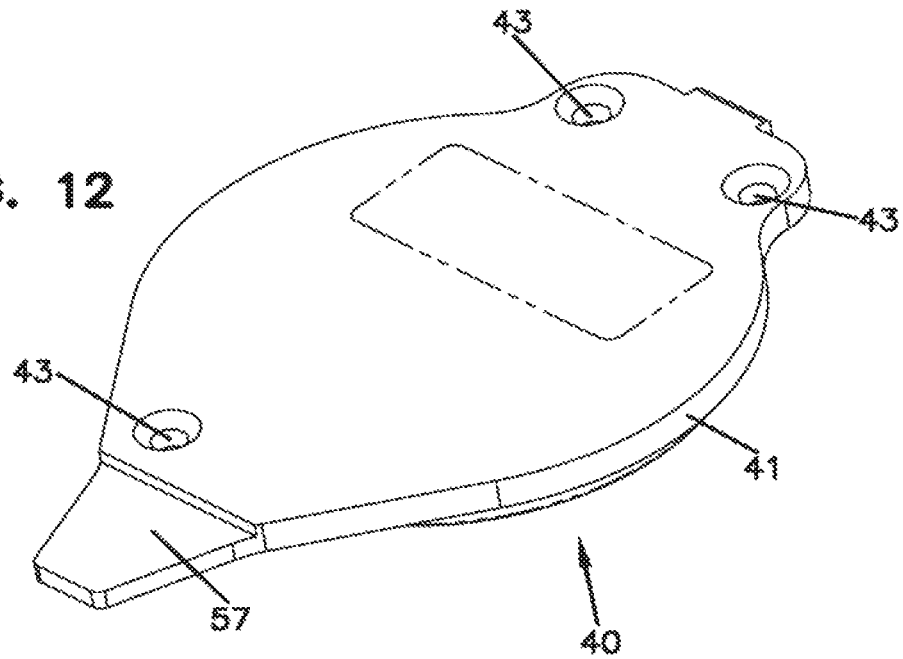
FIG. 12 is a bottom perspective view of the base of FIG. 11.
Figure 14:
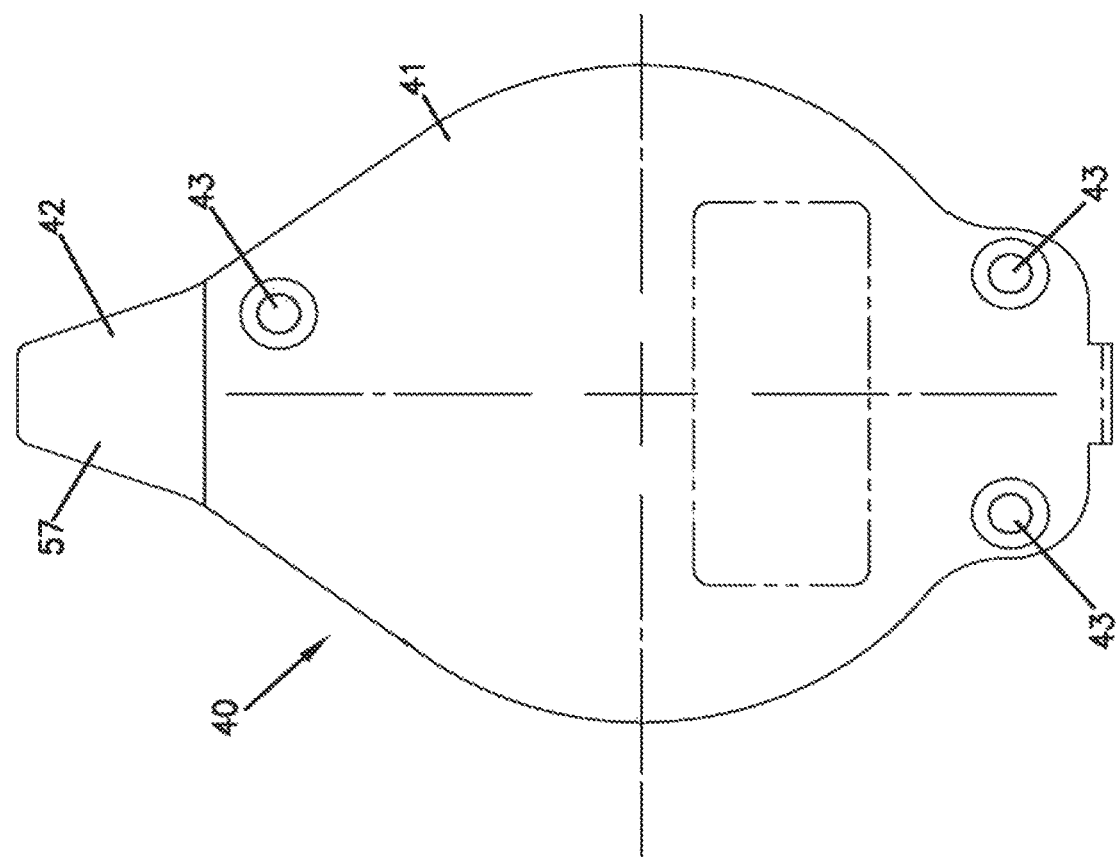
FIG. 14 is a bottom plan view of the base of FIG. 11.
Figure 13:
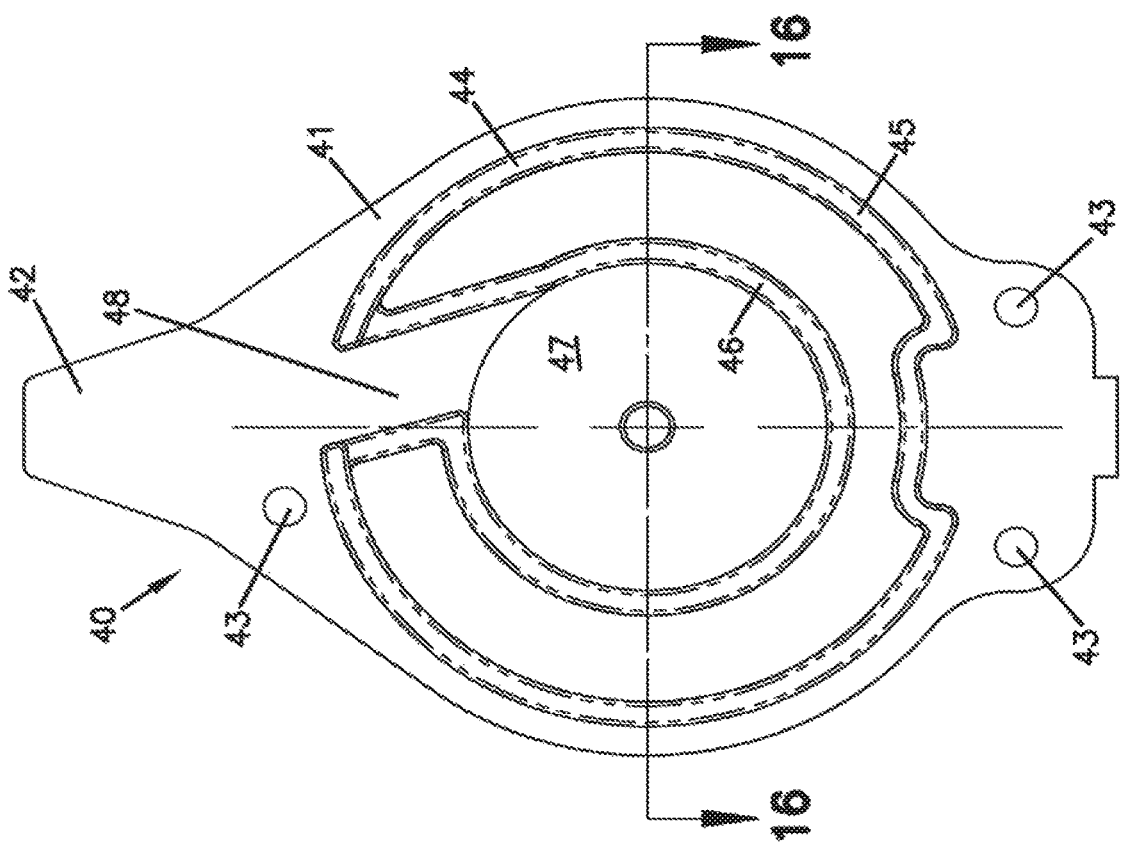
FIG. 13 is a top plan view of the base of FIG. 11.
Figure 15:
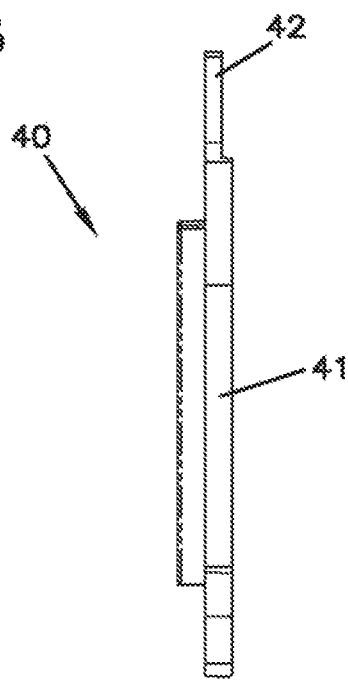
FIG. 15 is a side elevation view of the base of FIG. 11.
Figure 16:
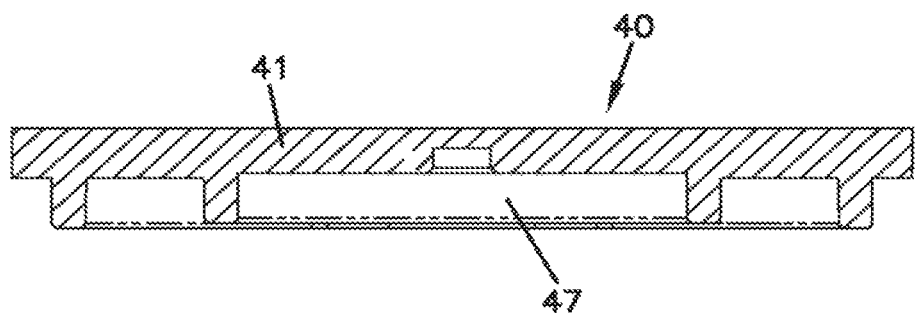
FIG. 16 is a cross-sectional view taken along line 16-16 of FIG. 13.

As illustrated in the bottom view of the base 40 in FIG. 12, the bottom side of the base 40 may include an indentation 57 configured to accommodate the thickness of a staple that may be mounted on an anchor 100 for securing the anchor 100 on the body.

Figure 28:
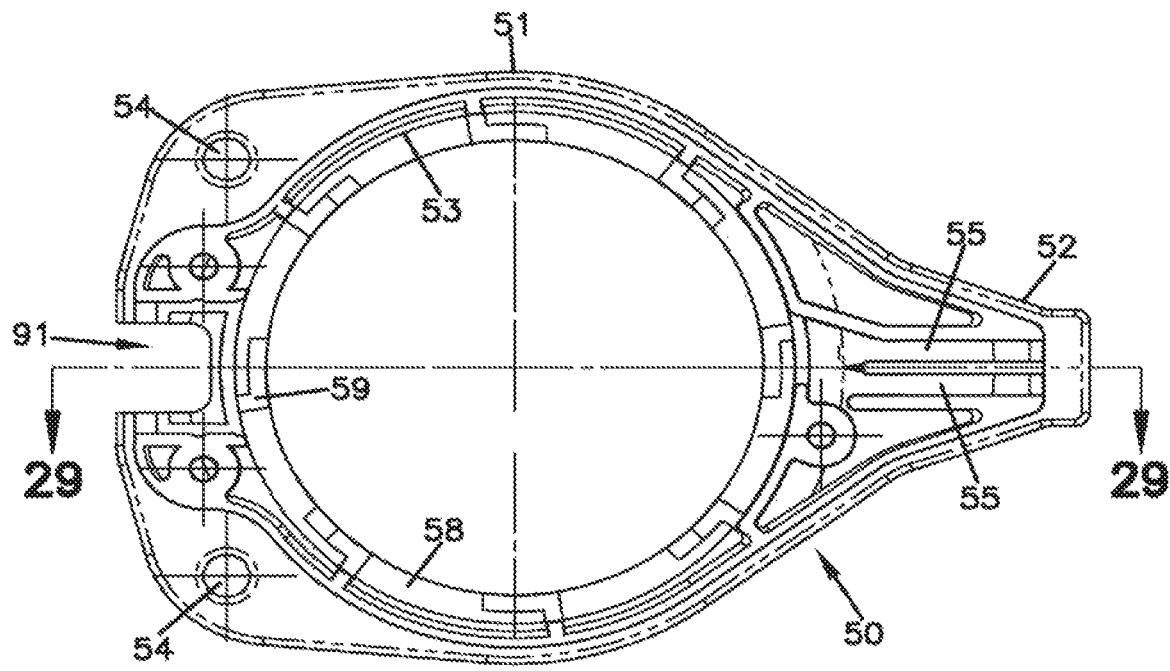
FIG. 28 is a bottom plan view of the cover of FIG. 25.
Figure 29:
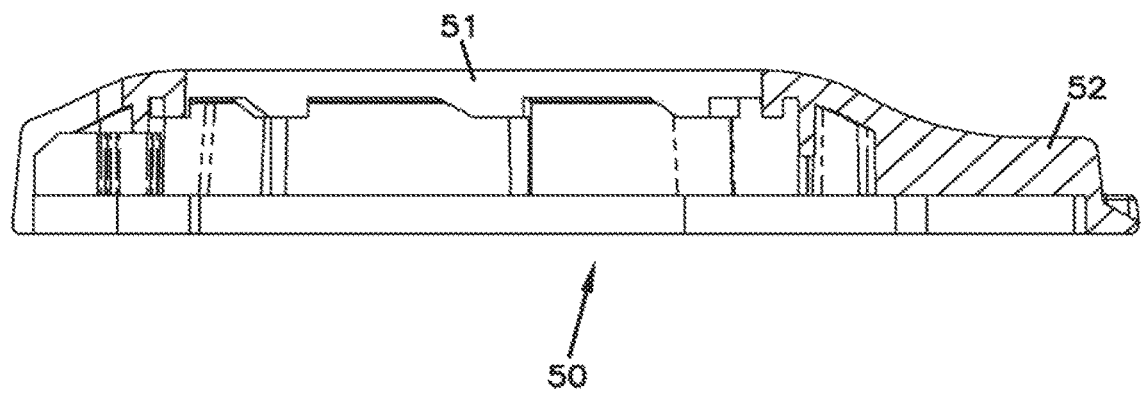
FIG. 29 is a cross-sectional view taken along line 29-29 of FIG. 28.
Figure 30:
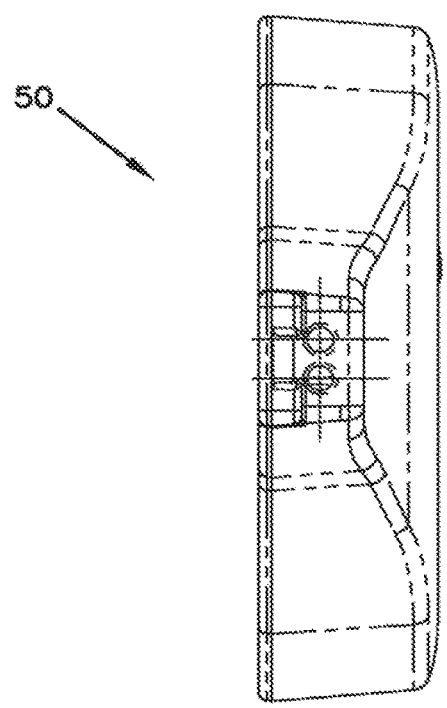
FIG. 30 is a front elevation view of the cover of FIG. 25.
Figure 31:
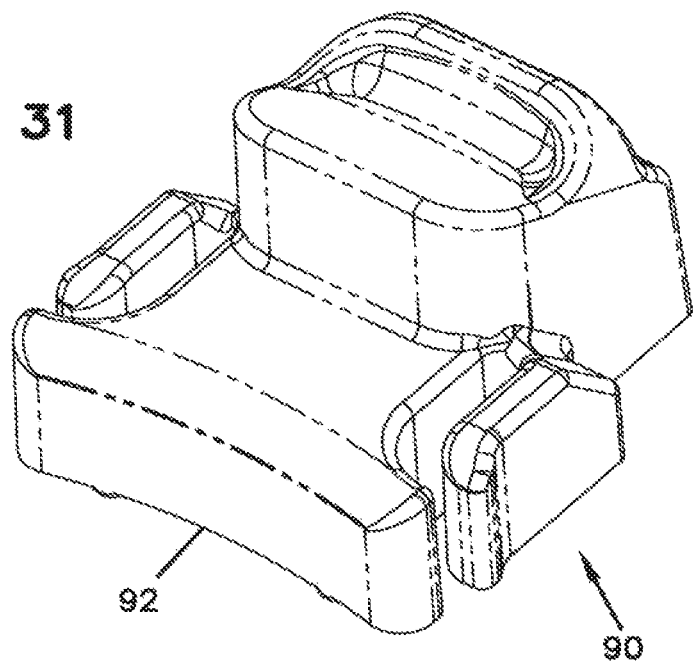
FIG. 31 is a top perspective view of a lock button of the tensioning apparatus of FIG. 3.
Figure 32:
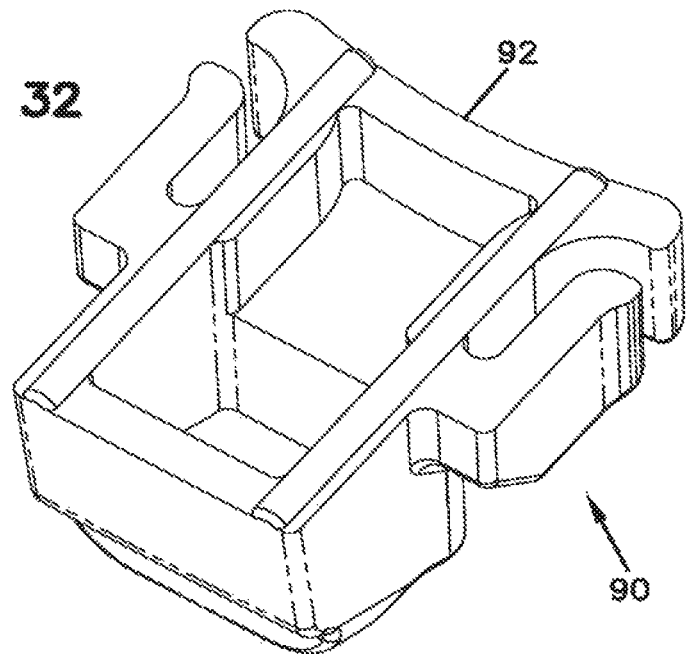
FIG. 32 is a bottom perspective view of the lock button of FIG. 31.
Figure 33:
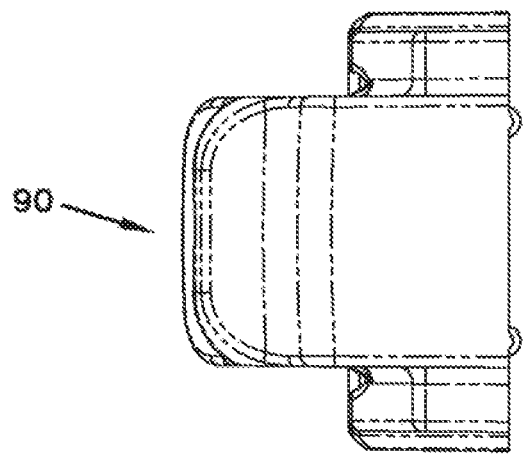
FIG. 33 is a rear elevation view of the lock button of FIG. 31.
Figure 34:
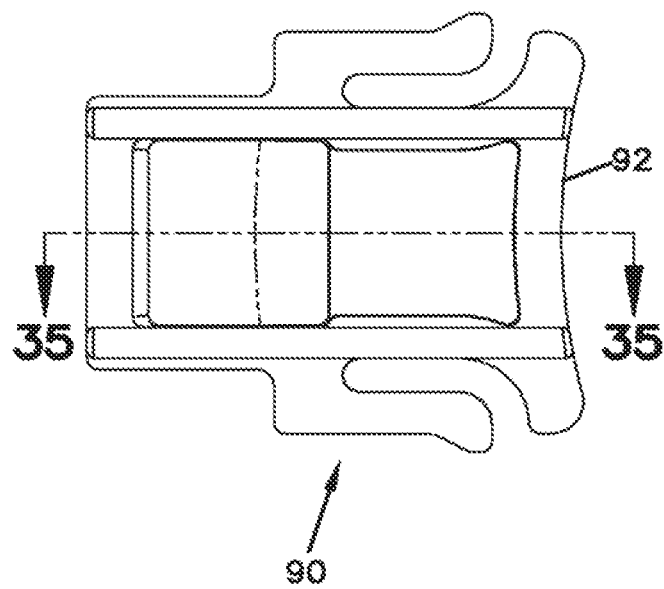
FIG. 34 is a bottom plan view of the lock button of FIG. 31.
Figure 35:
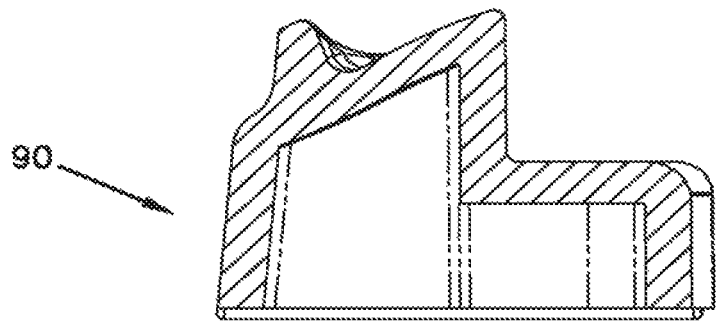
FIG. 35 is a cross-sectional view taken along line 35-35 of FIG. 34.

As seen in the bottom perspective view of the cover 50 in FIG. 26 and in the bottom plan view of the cover 50 in FIG. 28, the inner wall 53 of the cover 50 defines a flange 58 surrounding the inner perimeter of the main body portion 51. The flange 58 is adapted to trap the flange 68 of the knob 60 to capture the knob 60 in between the base 40 and the cover 50 of the tensioning apparatus 18. The flange 58 of the cover 50 defines ramped tabs 59 located around the periphery thereof that are adapted to slide over the ramped surfaces 71 of the horizontal tabs 69 of the knob 60 and fit into the rectangular gaps 73 defined between the horizontal tabs 69 as the knob 60 is turned clockwise, as will be described in further detail below. Although the cover 50 is shown as being coupled to the base 40 by fasteners, it may be coupled to the base 40 by various other methods including friction fit, by adhesives, by a snap fit, etc.

The cover 50 may also include a cutout 91 at the rear for accommodating a locking button 90 that can be used to lock the knob 60 with respect to the cover 50 and prevent relative rotation thereinbetween, as will be discussed in further detail below.

Referring now to FIGS. 31-35, the locking button 90 of the tensioning apparatus 18 is illustrated. The locking button 90 can be used to lock the knob 60 with respect to the rest of the tensioning apparatus 18 to prevent any unwanted rotation of the knob 60. The locking button 90 is seated within the cutout 91 of the cover 50 between the cover 50 and the knob 60 and is slidably movable in a linear fashion between a forward locking position and a rearward unlocking position.

In the forward locking position, the front portion 92 of the locking button 90 becomes seated underneath the flange 68 of the knob 60 and prevents the knob 60 from being pushed downwardly with respect to the cover. Since rotating the knob 60 clockwise causes the rectangular tabs 59 on the inside of the cover 50 to ride up and over the ramped surfaces 71 of the horizontal tabs 69 of the knob 60, the knob 60 has to travel downwardly in order to be turned in the clockwise direction. A clicking sound may be heard as the rectangular tabs 59 are seated into the rectangular gaps 73 as they ride up and over the ramped surfaces 71. The front portion 92 of the locking button 90 prevents this downward movement of the knob 60, preventing the rotation of the knob 60 in the clockwise direction.

Regarding the counterclockwise direction, the interlocking of the rectangular tabs 59 within the rectangular gaps 73 normally prevents the knob 60 from turning backwards in a counterclockwise direction. For the knob 60 to be rotated in the counterclockwise direction, the knob 60 needs to pressed downwardly with respect to the cover 50, wherein the tabs 59 located around the periphery of the flange 58 of the cover 50 are freed from the rectangular gaps 73 defined between the horizontal tabs 69 of the knob 60, allowing the knob 60 to be turned counterclockwise and unwind the line 12, 22. However, as noted above, the front portion 92 of the locking button 90 prevents this downward movement of the knob 60.

When the locking button 90 is slid rearwardly to the unlocking position, the front portion 92 is removed from underneath the flange 68 of the knob 60, allowing the knob to be moved down with respect to the cover and rotated in either direction.

C. Tension Line and Barbed Suture

As discussed previously, the wound closure system 10 may include a tension line 22 that is wound around the spool 20 of the tensioning apparatus 18 and that is coupled to the barbed suture line 12 that is sutured to body tissue around the periphery of the wound 14. Such a tension line 22 may be a nylon or polypropylene line, string, a cable, a wire, or other similar item. The tension line 22 may be sufficiently flexible and bendable to allow winding around the spool 20 within the tensioning apparatus 18. One embodiment of such a tension line 22 is made from nylon and has a tensile strength of about six lbs to ten lbs. The tension line 22 may include a thread diameter of about 0.5 mm to 0.6 mm.

As discussed before, although depicted as including a separate tensioning apparatus 18 in FIGS. 1-2, the wound closure system 10 may instead simply utilize an elastic line 22 that is connected to the barbed suture line 12 or an elastic barbed suture line 12 itself to provide the dynamic tension on the body tissue surrounding the wound 14. An elastic line or elastic suture line can also be used in combination with a separate tensioning apparatus such as the tensioning apparatus 18.

With the use of a separate tension apparatus 18, the tension line 22 and/or the barbed suture line 12 may be inelastic since the tensioning apparatus 18 provides the dynamic or continuous force needed for wound closure.

Regarding the barbed suture 12, as noted above and illustrated in FIGS. 1 and 2, the barbed suture line 12 includes a plurality of barbs 13 distributed around the circumference of the suture line 12. Suturing needles 16 may be provided at the ends of the barbed suture line 12 to facilitate suturing to body tissue. As shown in FIG. 2, once the barbed suture line 12 has been sutured around the wound area 14, the needles 16 may be removed and the ends tied together to form a closed loop around the wound area 14.

According to one embodiment of the suture line 12 of the wound closure system 10, the barbs 13 of the suture line 12 may be unidirectional such that all of the barbs 13 extend out at an acute angle along the same direction with respect to the longitudinal axis of the suture line 12. It is also contemplated that the suture line 12 could be provided with two sections of barbs 13, wherein all the barbs 13 in the first section extend out at an acute angle in a first direction and all the barbs 13 in the second section extend out at an acute angle in a second opposite direction. Such suture lines 12 can be used, for example, when body tissue on opposing sides of a wound 14 are sutured starting from the same point going to the opposite end of the wound 14.

The barbs 13 of the barbed suture 12 may be flexible such that, when suturing, they elastically flex inwardly toward the line surface to facilitate passing through body tissue. When a barb 13 passes through the body tissue and comes out the other side of the body tissue, the barb 13 may flex again outwardly from the suture line surface to provide a catch and grabs the body tissue if the suture 12 is pulled in the opposite direction. In this manner, the barbed suture 12 can be sutured through the body tissue as in a conventional suture, however, preventing any back-up of the suture 12 once passed through body tissue.

The barbs 13 may be distributed individually in a 360° fashion around the periphery of the suture line 12, with gaps provided between each of the barbs 13. According to other example embodiments of barbed sutures, instead of the barbs 13 being individually distributed around the suture line, the barbs 13 may be grouped together, wherein a first group of barbs 13 may be located at a first radial location on the suture line 12, a second group of barbs 13 may be located at a spaced second radial location on the suture line 12 (for example, on an opposite side of the suture line 12 from the first group, etc.), and so forth.

As noted previously, the wound closure system 10 and the barbed suture line 12 can be set up such that the tension force is applied in either direction with respect to the barbs 13. If the tension is applied with the direction of the barbs 13, the barbed suture 12 operates in a similar manner to a conventional suture and slides through the body tissue to pull the sides of the body tissue toward or over the open wound area 14. During this type of a suture set-up, the barbs 13 still play a role during the initial suturing of the body tissue by preventing back-up of the suture line 12. If the wound closure system 10 is used such that tension is applied against the direction of the barbs 13, the tissue is stretched toward or over the open wound area 14 by the grabbing action of the barbs 13.

One example embodiment of a barbed suture line 12 that is suitable for use with the wound closure system 10 of the present disclosure is manufactured by Covidien and marketed under the name "V-Loc™ 180 Absorbable Wound Closure Device". Another example embodiment of a barbed suture line 12 that is suitable for use with the wound closure system 10 of the present disclosure is available from Angiotech Pharmaceuticals, Inc. under the model name "Quill® SRS Self-Retaining System".

As noted above, the barbed suture line 12 may be attached directly to the tensioning apparatus 18 of the wound closure system 10 or may be attached thereto with a separate tension line 22 that is pre-wound around the spool 20 of the tensioning apparatus 18. One example method of attaching the barbed suture line 12 to a tension line 22 that is already wound within the tensioning apparatus 18 is shown in FIGS. 40-42. As shown in FIGS. 40-42, according to one embodiment, the barbed suture line 12 may include a ball structure 24 crimped to the end thereof. The end that includes the crimped ball structure 24 could be the end with the needle 16 or it could be the opposite end. The tension line 22 that is pre-wound around the spool of the tensioning apparatus may include a socket structure 26 crimped to the end of the tension line 22. The socket structure 26 acts as a receiver for the ball structure 24 in connecting the barbed suture line 12 to the tension line 22 in a quick and easy manner. Other methods of attachment may be used in attaching the barbed suture line 12 to a separate tension line 22 wrapped around the spool 20 of the tensioning apparatus 18 of FIGS. 3-5.

Use of a barbed suture line 12 for the wound closure system 10 provides a number of advantages over prior art systems. Fever steps are needed in initial set-up of the wound closure system 10. Use of body anchors 100 and staples may be eliminated for the wound closure system 10. The barbed suture line 12 that is used in initially stretching the body tissue can also be used for final closure of the wound 14 instead of having to resuture the wound 14 after stretching. The physician can simply pull the barbed suture line after the body tissue surrounding the wound has been stretched to close the wound. Due to the barbs, tying the ends of the suture line is not necessary. Surgeons are generally familiar with the suturing process so this type of a system provides less of a paradigm shift for surgeons in setting up the wound closure system 10.

D. General Use of Wound Closure System

Figure 2A:
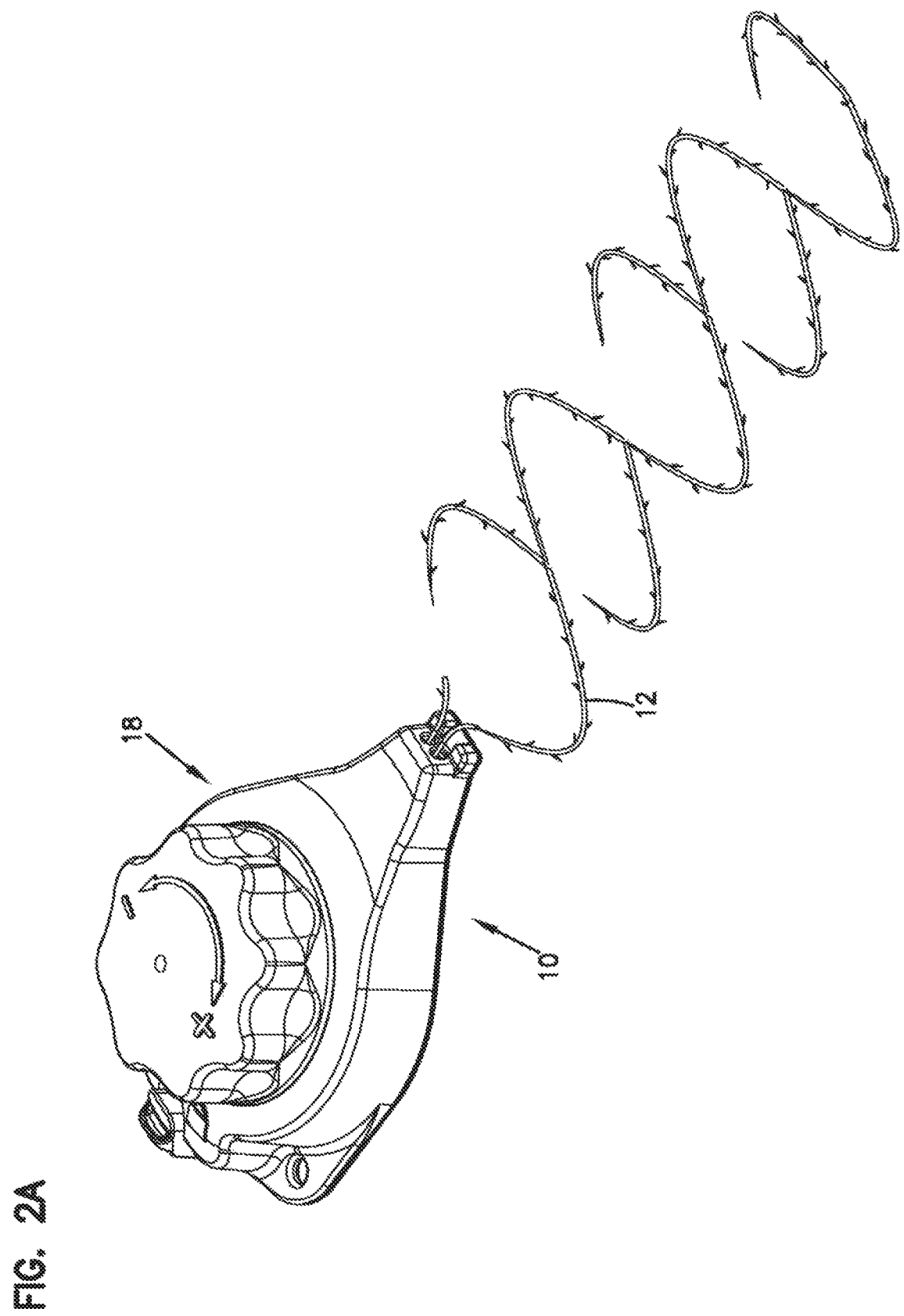
FIG. 2A illustrates the wound closure system of FIG. 1 in operation in an alternative arrangement adjacent the wound area.

The tensioning apparatus 18 of the wound closure system 10 of the present disclosure is used in a manner similar to that shown and described in U.S. Pat. No. 7,455,681, the entire disclosure of which has been incorporated herein by reference. For example, according to one example method, before applying dynamic or continuous tension to stretch the tissue, the barbed suture line 12 may be sutured to body tissue surrounding the wound area 14. The suturing may occur as shown in FIG. 2, wherein the suture 12 is passed in and out of the body tissue around the wound 14. As discussed previously, there are a number of possibilities on the types of barbed suture line(s) that could be used and the direction of suturing. One or more barbed suture lines 12 can be used and attached directly to the spool 20 of the tensioning apparatus 18. In other embodiments, the barbed suture lines 12 may be indirectly attached to the tensioning apparatus 18 with the use of a pre-attached tension line 22. As described, a ball/socket type of an attachment arrangement can be used. In suturing the barbed suture 12, a single suture line, one end of which is attached to the tensioning apparatus 18, can be sutured to the body tissue and the other end tied again to the tensioning apparatus 18. According to other methods, two separate barbed suture lines 12 that are attached to the tensioning apparatus 18 can be sutured to body tissue starting from the same point going to the opposite end of the wound 14, wherein the ends of the lines 12 would be tied to form a closed loop. As noted above, the direction of the application of the tension may be along the direction of the barbs 13 or opposite the direction of the barbs 13. Both methods are effective in stretching the body tissue for wound closure. A single barbed suture line 12 that has bidirectional barbs 13 can also be used. Such a barbed suture line 12 might include suture needles 16 at both ends of the line 12, as shown in FIG. 1, wherein the middle portion of the line 12 where the barbs 13 change direction can be attached to the spool 20 of the tensioning apparatus 18. According to one embodiment, the barbed suture line 12 may extend around substantially the entire periphery of the wound 14 and application of tension to the suture line 12 draws and stretches the body tissue toward the wound 14 (see FIG. 2). According to another embodiment, the suture line 12 can also be sutured to the body tissue surrounding the wound 14 in a manner so as to extend across the wound 14, i.e., in a "shoe-lace" configuration in use of the wound closure system 10 (see FIG. 2A). It should also be noted that although the wound closure system 10 of the present disclosure has been illustrated with a single tensioning apparatus 18, more than one tensioning apparatus 18 can be used. For example, two tension apparatuses 18, one on each side of a generally elongate wound 14, can be used. In one example variation of such a set-up, a barbed suture line 12 from one tensioning apparatus 18 may be sutured in one direction and a barbed suture line 12 from the other tensioning apparatus 18 may be sutured in the opposite direction, wherein tension applied by the two tensioning apparatuses 18 would cause the barbs 13 to grab the tissue and pull both sides of the tissue inwardly toward the wound 14.

In certain embodiments, a wound closure system having two barbed suture lines, wherein one suture line would go into the deep dermis/subcutaneous layer and the second suture line would go into the dermal/subcuticular layer to provide a two-layer closure, could be implemented.

It should be noted that the above described set-up arrangements are simply examples and other arrangements can certainly be used in setting up the wound closure system 10 of the present disclosure.

In assembling the tensioning apparatus 18, according to one specific example embodiment, after one or two barbed suture line(s) 12 has been attached to the spool 20 either directly or indirectly through the openings 5 and 7 and wound around the spool 20, the tensioning apparatus 18 may be assembled with the spool 20 fitting into the base 40. After winding of the tension line 22 or the barbed suture line 12, the biasing member 30 is placed on top of the spool 20, the knob 60 is placed on top of the biasing member 30 after the dowel pin 80 and the linear spring 70 are placed within the well 19 of the spool 20. The cover 50 is then mounted on top of the base 40 trapping the knob 60 therebetween the base 40 and the cover 50 and the line(s) 12, 22 guided out of the snout portion 52 of the cover 50. After assembly, the barbed suture lines 12 that are attached to the tensioning apparatus 18 can be sutured to body tissue starting from the same point going to the opposite end of the wound 14, wherein the ends of the lines 12 can be tied to form a closed loop. There should be enough line 12 let-out initially to perform the suturing operation.

After the barbed suture line(s) 12 is sutured to body tissue and the loop closed, the knob 60 of the tensioning apparatus 18 may be turned clockwise to wind the biasing member 30 located therewithin and start pulling in the barbed suture line 12.

Rotating the knob 60 clockwise causes the rectangular tabs 59 on the inside of the cover 50 to ride up and over the ramped surfaces 71 of the horizontal tabs 69 of the knob 60. The linear spring 70 protruding out of the spool 20 is used to exert an upward force on the knob 60 to keep the horizontal tabs 69 of the knob 60 pressed against the flange 58 of the cover 50. A clicking sound may be heard as the rectangular tabs 59 are seated into the rectangular gaps 73 as they ride up and over the ramped surfaces 71. The interlocking of the rectangular tabs 59 within the rectangular gaps 73 prevents the knob 60 from turning backwards in a counterclockwise direction.

When the knob 60 is turned clockwise, the biasing member 30 is loaded because the outer tab portion 33 of the coiled band 31 fits into one of the vertical indents 65 causing the biasing member 30 to turn with the knob 60. When the coiled band 31 is initially in an unwound orientation, the large diameter of the band 31 creates a tight fit with the interior surface 64 of the knob 60 creating a substantial amount of friction with the interior surface 64 of the knob 60. In this manner, the outer tab portion 33 is kept pressed against the inner surface 64 of the knob 90, within one of the vertical indents 65. As the biasing member 30 is wound, it becomes smaller and eventually obtains a diameter small enough that the outer tab 33 no longer exerts enough friction force against the interior surface 64 of the knob 60. At this point, further winding of the knob 60 causes the outer tab portion 33 to slip out of the vertical indents 65. This slipping makes an audible sound and gives an indication that the biasing member 30 is fully wound.

Since the spool 20 is connected to the biasing member 30, turning of the knob 60 also causes turning of the spool 20, tightening the barbed suture line 12 around the wound area 14. The biasing member 30 is wound to such extent that it applies a dynamic force on the barbed suture line 12 pulling the body tissue toward the wound 14. The design of the snout 52 of the cover 50 makes it possible to concentrate all the pulling force into one area. The snout 52 also inhibits any pulling on the tensioning apparatus 18 because the tip of the snout 52 aligns the tensioning apparatus 18 with the loop of the barbed suture line 12 around the periphery of the wound 14 diverting all the tension forces to a transverse direction along the loop instead of in the direction of the snout 52 itself. As the tissue is stretched toward the wound 14, the wound-up biasing member 30 and hence the spool 20 keeps the barbed suture line 12 taut. It should be noted that if the tension is being applied in the direction of the barbs 13, the biasing member 30 causes the barbed suture line 12 to slide through the body tissue as the body tissue is stretched. If the tension is being applied opposite to the direction of the barbs 13, the biasing member 30 causes the barbs 13 to catch the body tissue and stretch the body tissue by the grabbing action.

Occasionally it may be necessary to release the barbed suture line 12 to resuture or reposition it for adjustments or to remove the tensioning apparatus 18. Pushing down on the knob 60 causes the linear spring 70 (see FIGS. 4 and 5) to compress and the rectangular tabs 59 on the inside of the cover 50 to disengage from the rectangular gaps 73 defined around the knob 60. This causes the knob 60 to be able to be turned backwards in the counterclockwise direction and the barbed suture line 12 to come out.

During use, the locking button 90 may be used to lock the knob 60 with respect to the rest of the tensioning apparatus 18 to prevent any unwanted rotation of the knob 60.

The above specification provides examples of how certain inventive aspects may be put into practice. It will be appreciated that the inventive aspects can be practiced in other ways than those specifically shown and described herein without departing from the spirit and scope of the inventive aspects.

We claim:

1. A wound closure system comprising:
    a suture line adapted to be sutured through body tissue adjacent an open wound, the suture line adapted to be sutured so as to pass into the body tissue at an entry point and exit at an exit point, the suture line including a plurality of barbs extending outwardly at an acute angle with respect to a surface of the suture line; and
    a housing that houses a biasing member that is adapted to apply a continuous pulling force on the suture line for stretching the body tissue toward the open wound, wherein the biasing member is configured to take up any slack of the suture line during stretching of the body tissue and keep the suture line taut.

2. The wound closure system of claim 1, wherein the suture line includes at least one needle at an end of the suture line.

3. The wound closure system of claim 1, wherein the suture line is a unidirectional suture line such that the plurality of barbs extend outwardly at the acute angle along the same direction with respect to a longitudinal axis of the suture line.

4. The wound closure system of claim 3, wherein the plurality of barbs are configured to be flexible so as to flex toward the surface of the suture line when a respective barb enters the body tissue and flex outwardly away from the surface of the suture line when the respective barb exits the body tissue.

5. The wound closure system of claim 1, wherein the plurality of barbs includes a first set of barbs and a second set of barbs, the first set of barbs extending outwardly at a first acute angle in a first direction, and the second set of barbs extending outwardly at a second acute angle in a second direction.

6. The wound closure system of claim 5, wherein the plurality of barbs are configured to be flexible so as to flex toward the surface of the suture line when a respective barb enters the body tissue and flex outwardly away from the surface of the suture line when the respective barb exits the body tissue.

7. The wound closure system of claim 5, wherein the first direction is opposite the second direction.

8. The wound closure system of claim 1, wherein the biasing member includes a spring.

9. The wound closure system of claim 8, wherein the housing including a spool rotatably coupled to the housing, the spool coupled to the spring and adapted for winding the spring for the application of the continuous pulling force on the suture line.

10. The wound closure system of claim 9, wherein the housing and the spring include intermating structures adapted for winding the spring, wherein the intermating structures are adapted to slip with respect to each other when the spring has been fully wound to provide an indication that the spring is fully wound.

11. The wound closure system of claim 10, wherein the intermating structures include radially arranged vertical indents formed within the housing and a radially outwardly projecting tab of the spring.

12. The wound closure system according to claim 11, wherein the radially arranged vertical indents are formed within a knob of the housing.

13. The wound closure system of claim 12, wherein the housing includes a locking button that is adapted to prevent rotation of the knob with respect to the housing.

14. The wound closure system of claim 13, wherein the locking button is adapted to be pushed along a longitudinal direction of the spool to release the continuous pulling force.

15. A method of reducing the size of an open wound by pulling body tissue adjacent the open wound toward or over the open wound, the method comprising:
    suturing a suture line through the body tissue adjacent the open wound so as to pass into the body tissue at an entry point and exit at an exit point, the suture line including a plurality of barbs extending outwardly at an acute angle with respect to a surface of the suture line; and
    providing housing that houses a biasing member that continuously applies a pulling force on the suture line to stretch the body tissue toward or over the open wound, wherein the continuous pulling force is automatically applied by the biasing member during stretching of the body tissue.

16. The method of claim 15, wherein the suture line includes at least one needle at an end of the suture line.

17. The method of claim 16, further comprising suturing the line with the at least one needle through the body tissue in a shoe-lace configuration wherein at least a portion of the suture line crosses the open wound at least twice.

18. The method of claim 15, wherein the biasing member is a spring, and wherein the housing including a spool rotatably coupled to the housing, the spool coupled to the spring and adapted for winding the spring for the application of the continuous pulling force on the suture line, and wherein a knob of the housing and the spring include intermating structures adapted for winding the spring, wherein the intermating structures are adapted to slip with respect to each other when the spring has been fully wound to provide an indication that the spring is fully wound.

19. The method of claim 18, wherein the housing includes a locking button that is adapted to prevent rotation of the knob with respect to the housing.

20. The method of claim 19, further comprising locking the locking button to prevent rotation of the knob with respect to the housing.

* * * * *